(12) United States Patent
Wagner et al.

(10) Patent No.: US 12,644,890 B2
(45) Date of Patent: Jun. 2, 2026

(54) METHODS AND DEVICES FROM ISOLATION OF TUMOR CELLS

(71) Applicant: ORBIS HEALTH SOLUTIONS, LLC, Greenville, SC (US)

(72) Inventors: Thomas E. Wagner, Greenville, SC (US); Amanda J. Sloan, Greenville, SC (US); Xianzhong Yu, Mauldin, SC (US)

(73) Assignee: Elios Holdings, LLC, Austin, TX (US)

( * ) Notice: Subject to any disclaimer, the term of this patent is extended or adjusted under 35 U.S.C. 154(b) by 0 days.

(21) Appl. No.: 19/199,750

(22) Filed: May 6, 2025

(65) Prior Publication Data

US 2025/0264386 A1 Aug. 21, 2025

Related U.S. Application Data

(63) Continuation of application No. PCT/US2024/028803, filed on May 10, 2024.

(60) Provisional application No. 63/466,172, filed on May 12, 2023.

(51) Int. Cl.
| | |
|---|---|
| *G01N 33/574* | (2006.01) |
| *G01N 1/40* | (2006.01) |
| *G01N 33/543* | (2006.01) |

(52) U.S. Cl.
CPC ..... *G01N 33/57492* (2013.01); *G01N 1/4077* (2013.01); *G01N 33/54313* (2013.01); *G01N 33/574* (2013.01)

(58) Field of Classification Search
CPC .......... G01N 33/54313; G01N 33/574; G01N 33/57492; G01N 1/4077
See application file for complete search history.

(56) References Cited

U.S. PATENT DOCUMENTS

2024/0245808 A1* 7/2024 Chen .................. A61K 41/0052

FOREIGN PATENT DOCUMENTS

| WO | WO-2012/142180 A1 | 10/2012 |
|---|---|---|
| WO | WO-2014/040089 A1 | 3/2014 |
| WO | WO-2023/274252 A1 | 1/2023 |

OTHER PUBLICATIONS

Deng et al. Dual Targeting with Cell Surface Electrical Charge and Folic Acid via Superparamagnetic Fe3O4@Cu2-xS for Photothermal Cancer Cell Killing. Cancers 13 (5275): pp. 1-19 (2021).*

(Continued)

*Primary Examiner* — Gailene Gabel
(74) *Attorney, Agent, or Firm* — Foley & Lardner LLP

(57) ABSTRACT
Described herein are methods and compositions for isolating cancer cells using positively charged surfaces, such as beads, microparticles, and capillary tubes. The methods and compositions for isolation can be used in cancer diagnosis, treatment, and therapeutic preparation.

18 Claims, 19 Drawing Sheets

500-600 μm
Densely Positively Charged
Glass Microspheres

Spaces and channels
between
500 micron spheres
is ~ 125 μm

Largest Blood
Cell (Monocyte)
is <25 μm

(56)　　　　　　References Cited

OTHER PUBLICATIONS

Le et al. Detection of cancer cells based on glycolytic-regulated surface electrical charges. Biophys Rep 5(1): 10-18 (2019).*

Bingdi Chen et al., "Targeting Negative Surface Charges of Cancer Cells by Multifunctional Nanoprobes", Theranostics, vol. 6, No. 11, Jan. 1, 2016, pp. 1887-1898.

International Search Report and Written Opinion on PCT/US2024/028803 mailed Sep. 17, 2024.

Shengming Wu et al., "Rapid Label-Free Isolation of Circulating Tumor Cells from Patients' Peripheral Blood Using Electrically Charged $Fe_3O_4$ Nanoparticles", Applied Materials & Interfaces, vol. 12, No. 4, Jan. 14, 2020, pp. 4193-4203.

* cited by examiner

|  Tube 1 | Tube 2 | Tube 3 | Tube 4 |
| Initial cell solution | Pass through | Wash 1 | Wash 2 |

| Tube 1 | Tube 2 | Tube 3 | Tube 4 |
| Initial cell solution | Pass through | Wash 1 | Wash 2 |

Tube 1
Initial cell solution

Tube 2
Pass through

Tube 3
Wash 1

Tube 4
Wash 2

Tube 1
Initial cell solution

Tube 2
Pass through

Tube 3
Wash 1

Tube 4
Wash 2

Tube 1
Initial cell solution

Tube 2
Pass through

Tube 3
Wash 1

Tube 4
Wash 2

500-600 μm
Densely Positively Charged
Glass Microspheres

Spaces and channels
between
500 micron spheres
is ~ 125 μm

Largest Blood
Cell (Monocyte)
is <25 μm

A

B

A

B

C

METHODS AND DEVICES FROM ISOLATION OF TUMOR CELLS

CROSS REFERENCE TO RELATED APPLICATIONS

This application is a continuation of International Application No. PCT/US2024/028803, filed May 10, 2024, which claims priority to and the benefit of U.S. Provisional Application No. 63/466,172, filed May 12, 2023. The contents of these applications are incorporated herein by reference in their entireties.

FIELD

The present disclosure relates generally to methods and functionalized microspheres and surfaces (e.g., capillary tubes) for binding cancer cells. More particularly, the disclosure relates to an isolation matrix of functionalized microspheres or capillaries, and columns comprising said isolation matrix, for removing cancer cells from a biological sample. The methods and compositions disclosed herein can be used for diagnosing or treating cancer, among other things.

BACKGROUND

A tumor is an abnormal growth of body tissue and can be cancerous (malignant) or noncancerous (benign). Tumors, particularly cancerous tumors, are a serious threat to human well-being and their detection in early stage is critical in order to obtain effective treatment or cure. However, it is a challenge for conventional tumor detection methods to detect cancer earlier than symptoms appear, or detect cancer at earlier stages of tumor metastasis. For example, conventional methods fail to identify about 40% of cancer patients who are in need of more or enhanced therapies. It is also important to detect any early signs of spread in cancer following cancer treatments to assess effectiveness of the treatment, as well as if and what follow-up treatment is needed. Conventional cancer detection techniques such as x-ray imaging and nuclear magnetic resonance (NMR) imaging fail to provide reliable information to the above critical applications.

Recent research and clinical studies have shown that cancer invasion to a human body may occur very early in tumor development. Early detection and early systemic therapies will result in a declining death rate from cancer. Metastasis, initiated by tumor cells transported through the circulation from the primary tumor to vital distant organs, is known to be the leading cause of cancer related deaths. The early spread of tumor cells to lymph nodes or bone marrow in peripheral blood is referred to as circulating tumor cells (CTCs or CTC). CTCs may still exist in a patient' peripheral blood even after the removal of the primary tumor.

CTCs are essential for establishing metastasis, and detection and isolation of CTCs is an important tool to assess the aggressiveness of a given tumor and its potential of subsequent growth at distant organs. Detection of CTCs can also represent an early and first detection of cancer in a patient. Specific and sensitive detection and isolation of CTCs can be used to identify the initial presence of cancer and the overall cancer development or metastasis status, survival possibility, and assessment of the therapeutic response. CTC removal from the blood of a patient may also be useful for treating certain cancers.

The current CTC detection and isolation based on molecular biomarkers has been hampered by limitations in specificity and sensitivity of the methods. Therefore, there is a need for new targeting strategies that explore other biophysical properties of cancer cells. Unlike the current CTC detection methods based on molecular biomarkers, the present disclosure is agnostic for the detection of any type of cancer cell.

SUMMARY OF THE DISCLOSURE

The present disclosure provides, functionalized microspheres and surfaces (e.g., capillary tubes) that can bind to cancer cells based on those cells negative charge and the opposite positive charge of the functional groups. As described herein, microspheres and capillary tubes, which may be made of glass or other materials, can be functionalized to In a first aspect, the present disclosure provides methods of removing cancer cells from a biological sample, comprising: a) passing a biological sample comprising cancer cells through an isolation matrix comprising functionalized microspheres; and b) collecting the biological sample that flows through the isolation matrix in a first aliquot, wherein the cancer cells bind to the isolation matrix.

In some embodiments disclosed herein, the functionalized microspheres are functionalized with a positively charged function group. In some embodiments, the functionalized microspheres are functionalized with amine, polyethylenimine (PEI), and/or guanidine groups. In some embodiments, the microspheres comprise glass, polymer, or resin. In some embodiments, the microspheres are between 500 μm and 600 μm in diameter.

In embodiments disclosed herein, the biological sample comprises blood. In some embodiments, the biological sample is obtained from a subject that has or is suspected of having cancer. In some embodiments, the cancer is a hematological cancer or comprises a solid tumor. Some embodiments disclosed herein comprise eluting the cancer cells bound to the isolation matrix into a second aliquot. Some embodiments comprise administering the first aliquot back into the subject. Some embodiments comprise detecting the presence or absence of a cancer cell in the biological sample. Some embodiments comprise lysing the eluted cancer cells to obtain a lysate. Some embodiments comprise incorporating the lysate into a cancer vaccine. Some embodiments comprise determining the mRNA copy number from the cancer cell lysate. In some embodiments, mRNA copy number is determined by quantitative RT-PCR. Some embodiments comprise calculating the number of cancer cells bound to the functionalized microspheres.

In one aspect, the present disclosure comprises a cancer vaccine prepared by a process comprising: a) contacting a biological sample comprising cancer cells with a positively charged surface, wherein the cancer cells bind to the positively charged surface; b) collecting the biological sample that flows through the isolation matrix in a first aliquot; c) lysing the cancer cells to obtain a cancer cell lysate in a second aliquot; and d) incorporating the cancer cell lysate into a yeast cell wall particle (YCWP).

In one aspect, the present disclosure provides methods of treating cancer in a patient, comprising extracting cancer cells from the patient's blood by passing the blood through an isolation matrix comprising functionalized microspheres that bind to cancer cells.

In some embodiments disclosed herein, the functionalized microspheres are functionalized with a positively charged function group. In some embodiments, the functionalized microspheres are functionalized with amine, polyethylenimine (PEI), and/or guanidine groups. In some embodiments, the microspheres comprise glass, polymer, or resin. In some embodiments, the microspheres are between 500 µm and 600 µm in diameter.

In some embodiments disclosed herein, the patient has a hematological cancer or a malignant cancer.

Some embodiments disclosed herein comprise eluting the bound cancer cells from the isolation matrix. Some embodiments disclosed herein comprise lysing the eluted cells to obtain a lysate and incorporating the lysate into a cancer vaccine for treating the patient.

In one aspect, the present disclosure provides methods of detecting a cancer cell in a patient, comprising: a) passing a biological sample from the patient through an isolation matrix of functionalized microspheres, wherein the functionalized microspheres bind cancer cells; b) eluting the cancer cells from the matrix; and c) detecting the presence or absence of a cancer cell in the biological sample.

In some embodiments disclosed herein, the patient has a hematological cancer or a malignant cancer.

In some embodiments disclosed herein, the functionalized microspheres are functionalized with a positively charged function group. In some embodiments, the functionalized microspheres are functionalized with amine, polyethylenimine (PEI), and/or guanidine groups. In some embodiments, the microspheres comprise glass, polymer, or resin. In some embodiments, the microspheres are between 500 µm and 600 µm in diameter.

In one aspect, the present disclosure provides a cancer cell isolation matrix comprising functionalized microspheres comprising a positively charged function group, wherein the functionalized microspheres bind cancer cells. In some embodiments disclosed herein, the functionalized microspheres are functionalized with a positively charged function group. In some embodiments, the functionalized microspheres are functionalized with amine, polyethylenimine (PEI), and/or guanidine groups. In some embodiments, the microspheres comprise glass, polymer, or resin. In some embodiments, the microspheres are between 500 µm and 600 µm in diameter.

In one aspect, the present disclosure provides kits for purifying cancer cells from a biological sample, comprising functionalized microspheres, wherein the functionalized microspheres bind cancer cells from the biological sample.

In one aspect, the present disclosure provides methods of preparing a column for cancer cell isolation, comprising: a) preparing an isolation matrix, wherein the isolation matrix comprises functionalized microspheres; and b) depositing the isolation matrix into a container with, wherein the container has an inlet and outlet. In some embodiments disclosed herein, the functionalized microspheres are functionalized with a positively charged function group. In some embodiments, the functionalized microspheres are functionalized with amine, polyethylenimine (PEI), and/or guanidine groups. In some embodiments, the microspheres comprise glass, polymer, or resin. In some embodiments, the microspheres are between 500 µm and 600 µm in diameter.

In some embodiments, preparing the functionalized microspheres comprises coating the microspheres with 5% 3-Aminopropyltriethoxysilane solution. In some embodiments, preparing the functionalized microspheres comprises coating the microspheres with a 5% silane coupling agent. In some embodiments, preparing the functionalized microspheres comprises coating the microspheres with polyethylenimine (PEI). In some embodiments, preparing the functionalized microspheres comprises coating the microspheres with aminoguanidine. In some embodiments, depositing the isolation matrix comprises depositing between 0.1 and 1 ml of functionalized microspheres into the container.

In one aspect, the present disclosure provides methods of removing cancer cells from a biological sample, comprising: a) passing a biological sample comprising cancer cells through a functionalized capillary tube; and b) collecting the biological sample that flows through the capillary tube in a first aliquot, wherein the cancer cells bind to the capillary tube. In some embodiments, the capillary tube is functionalized with amine, polyethylenimine (PEI), and/or guanidine groups.

In one aspect, the present disclosure provides methods of removing cancer cells from a biological sample, comprising contacting a biological sample comprising cancer cells with a positively charged surface, wherein the cancer cells bind to the positively charged surface. In some embodiments, the positively charged surface comprises functionalized with amine, polyethylenimine (PEI), and/or guanidine groups. In some embodiments, the positively charged surface is made of glass, polymer, or resin. In some embodiments, the positively charged surface is selected from a bead, a microparticle, a capillary tube, a blood collection tube, a microscope slide, and a microscope slide coverslip. In some embodiments, the biological sample comprises blood. In some embodiments, the cancer is a hematological cancer or comprises a solid tumor. In some embodiments, the biological sample is obtained from a subject that has or is suspected of having cancer.

In some embodiments, the method further comprises detecting the presence or absence of a cancer cell in the biological sample. In some embodiments, the method further comprises lysing the cancer cells to obtain a cancer cell lysate. In some embodiments, the method further comprises incorporating the cancer cell lysate into a cancer vaccine. In some embodiments, the method further comprises calculating the number of cancer cells bound to the positively charged surface.

In one aspect, the present disclosure provides a cancer vaccine comprising a yeast cell wall particle (YCWP) and a cancer cell lysate prepared as described herein.

In some embodiments, the YCWP is modified by capping with a silicate. In some embodiments, the silicate is selected from the group comprising tetraethylorthosilicate, tetramethlorthosilicate, tetrapropylorthosilicate, and tetrabutylorthosilicate. Some embodiments comprise one or more adjuvants, excipients and preservatives.

In one aspect, the present disclosure provides methods of delivering a vaccine to a subject comprising administering a vaccine as disclosed herein to the subject.

In one aspect, the present disclosure provides methods of treating or preventing cancer, comprising administering the vaccine as disclosed herein to a subject in need thereof.

Some embodiments comprise administering the vaccine subcutaneously, orally, or intravenously. Some embodiments comprise administering the vaccine to the dermis of the subject.

In one aspect, the present disclosure provides a method of treating cancer in a patient, comprising extracting cancer cells from the patient's blood by contacting the patient's blood with a positively charged surface, wherein the cancer cells bind to the positively charged surface, and returning the blood to the patient after contacting the positively charged surface. In some embodiments, the positively charged surface comprises functionalized with amine, polyethylenimine (PEI), and/or guanidine groups. In some embodiments, the positively charged surface is made of glass, polymer, or resin. In some embodiments, the positively charged surface is selected from a bead, a microparticle, a capillary tube, a blood collection tube, a microscope slide, and a microscope slide coverslip. In some embodiments, the biological sample comprises blood. In some embodiments, the cancer is a hematological cancer or comprises a solid tumor. In some embodiments, the biological sample is obtained from a subject that has or is suspected of having cancer.

In one aspect, the present disclosure provides methods of detecting a cancer cell in a subject, comprising removing cancer cells from a biological sample according to the methods disclosed herein, and detecting the presence or absence of a cancer cell in the biological sample. In some embodiments, the cancer is a hematological cancer, a cancer comprising a solid tumor, or a malignant cancer.

In one aspect, the present disclosure provides device for isolating cancer cells, comprising a positively charged surface that is comprises amine groups, polyethylenimine (PEI), guanidine groups, or any combination thereof. In some embodiments, the positively charged surface is made of glass, polymer, or resin. In some embodiments, the positively charged surface is selected from a bead, a microparticle, a capillary tube, a blood collection tube, a microscope slide, and a microscope slide cover.

The following drawings and detailed description are exemplary and explanatory, but it is not intended to be limiting.

7 bound SKOV3 ovarian cancer cells (Beads), and unbound SKOV3 ovarian cancer cells (SKOV3). Error bars show standard deviation of n=3.

Figure 17:
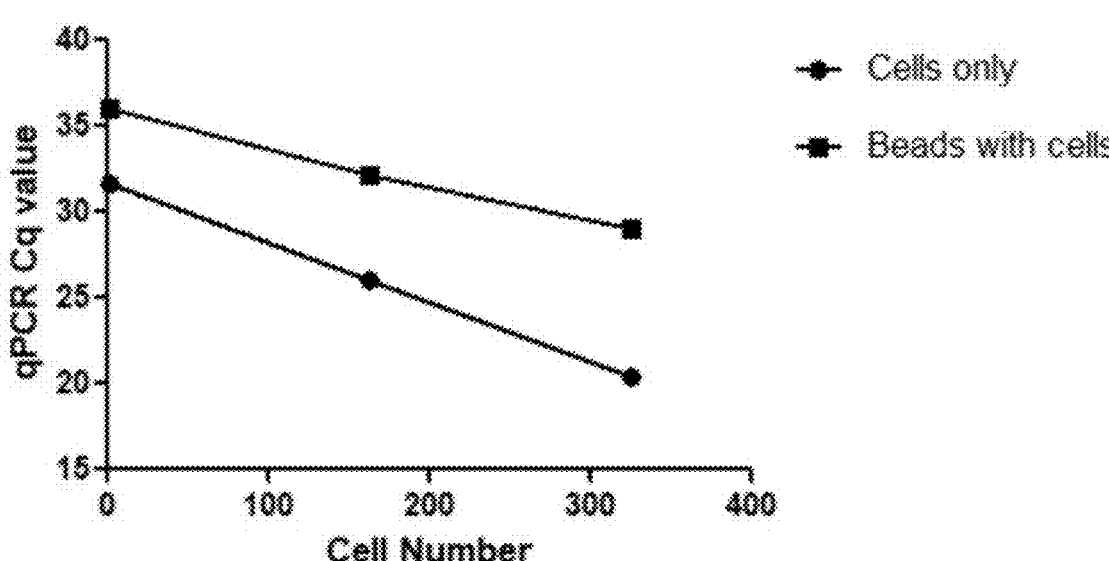

FIG. 17 shows a standard curve of number of cycles vs cell number produced using SK-BR-3 cells. The "Cells only" is a curve showing the SKOV3 cells vs CQ value as a standard curve. The "Beads with cells" is showing the number of cells bound to the bead vs the CQ value.

Figure 18:
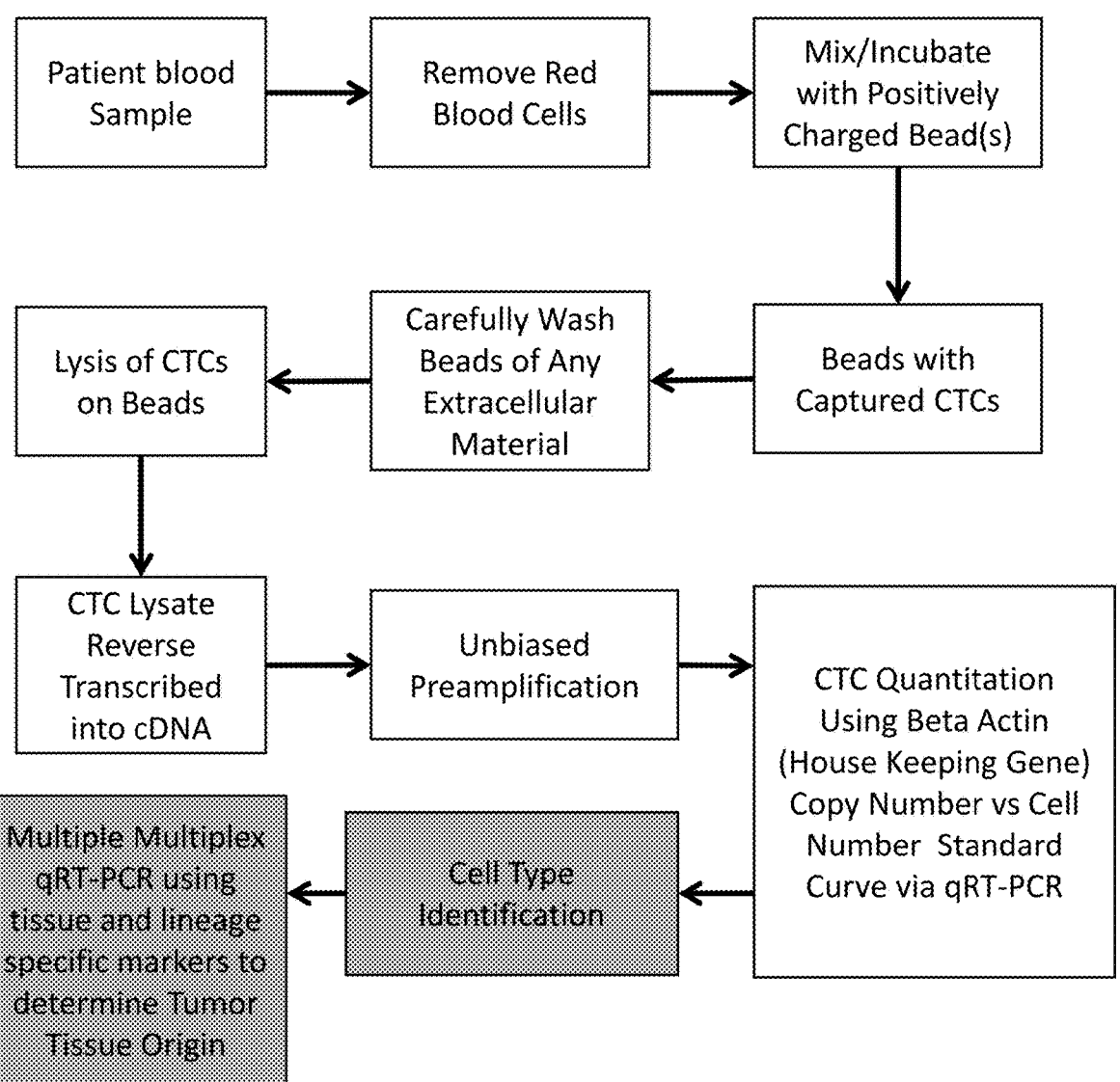

FIG. 18 shows one embodiment of the method used to quantify the number of cells in a sample (white boxes) and the method to detect and amplify circulating cancer cells in a patient (white and gray boxes).

Figure 19:
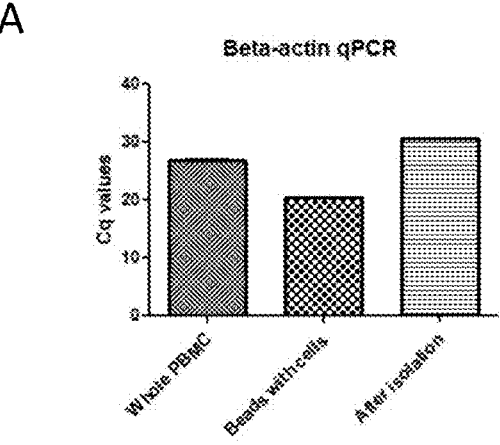
Figure 19:
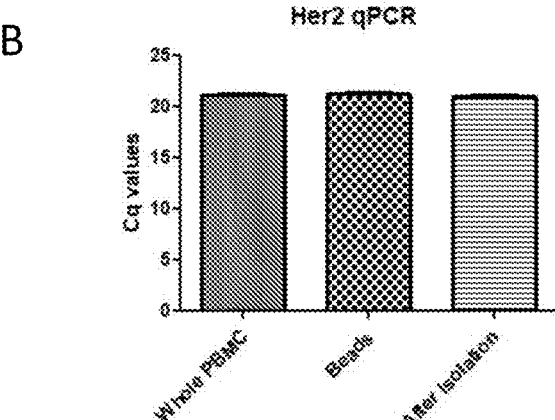
Figure 19:
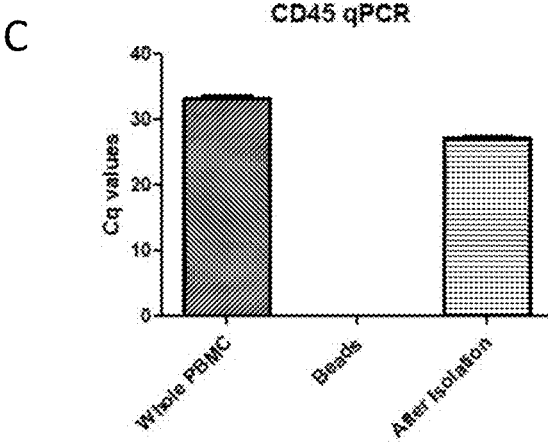

FIG. 19 shows number of PCR cycles to detect (A) beta-actin, (B) Her2, and (C) CD45 in the sample prior to incubation with the bead (Whole PBMC), bead bound breast cancer cells from a patient sample (Beads with cells/Beads), and the remaining cells from the patient sample that did not stick to the bead (After isolation). Error bars show standard deviation of n=3.

DETAILED DESCRIPTION

The present disclosure generally relates to the fields of cancer diagnosis and treatments, each of which utilize isolation of cancer cells from a biological sample (e.g., blood, plasma, or serum of a subject having or suspecting of having cancer). More particularly, the disclosure provides methods, compositions, and kits suitable for isolating cancer cells from a biological sample. The disclosed methods, compositions, and kits are based on the ability of positively charged surfaces, such as microparticles (e.g., glass microbeads) or capillary tubes, to capture negatively charged cancer cells.

Definitions

Unless otherwise defined, all technical and scientific terms used herein have the same meaning as commonly understood by one skilled in the art to which the present technology belongs.

As used herein, the term "about" refers to a stated numerical term and a value that is no more than 10% above or below the value being described. For example, the term "about 5 nM" indicates disclosure of both the stated value of 5 nM and a range of from 4.5 nM to 5.5 nM.

As used herein, the singular forms "a," "an," and "the" include plural referents unless the content clearly dictates otherwise. Thus, for example, a "microparticle" includes two or more microparticles, a "polynucleotide" includes two or more polynucleotides, an "cell" refers to two or more cells, and the like.

As used herein, the terms "particle", "bead", or "sphere" are used interchangeably and may comprise any shape or composition. A particle, bead, or sphere may have any diameter greater than 1 mm. In some embodiments, a particle, bead, or sphere may have a diameter greater than 1 mm, greater than 1.5 mm, greater than 2 mm, greater than 2.5 mm, or greater than 3 mm. In some embodiments, a particle, bead, or sphere may have a diameter between 1 mm 10 mm. In some embodiments, a particle, bead, or sphere may have a diameter between 1.5 mm and 5 mm. In some embodiments, a particle, bead, or sphere may have a diameter between 1.7 mm and 2.5 mm. In some embodiments, a particle, bead, or sphere may have an average diameter of about 1 mm, about 1.5 mm, about 1.7 mm, about 2 mm, about 2.5 mm, about 3 mm, about 5 mm, about 7.5 mm, about 10 mm, about 15 mm, or about 20 mm. In some embodiments, the particle, bead, or sphere is solid. In some embodiments, the particle, bead, or sphere is hollow. In some embodiments, the particle, bead, or sphere is porous or non-porous. In some embodiments, the particle, bead, or sphere comprises one or more different materials. In some embodiments, the particle, bead, or sphere comprises or consists of glass, nylon, hydrogel, ceramic, metal and/or any other suitable material. In some embodiments, the particle, bead, or sphere is magnetic. In some embodiments, the particle, bead, or sphere is coated with a metallic surface such as nickel. In some embodiments, the particle, bead, or sphere is functionalized.

As used herein, the term "microparticle" refers to a particle of any shape or composition having a diameter between 1 μm and 1000 μm. In some embodiments, a microparticle has a diameter between 200 μm and 800 μm. In some embodiments, a microparticle has a diameter between 400 μm and 600 μm. In some embodiments, a microparticle has an average diameter of about 1 μm, about 100 μm, about 200 μm, about 300 μm, about 400 μm, about 500 μm, about 600 μm, about 700 μm, about 800 μm, about 900 μm, or about 1000 μm. In some embodiments, the microparticle is solid. In some embodiments, the microparticle is hollow. In some embodiments, the microparticle is porous or non-porous. In some embodiments, the microparticle comprises one or more different materials. In some embodiments, the microparticle comprises or consists of glass, nylon, hydrogel, ceramic, metal and/or any other suitable material. In some embodiments, the microparticle is magnetic. In some embodiments, the microparticle is coated with a metallic surface such as nickel. In some embodiments, the microparticle is functionalized. In some embodiments, the microparticle may be a microsphere or a nanoparticle.

As used herein, the term "matrix" refers to a collection of microparticles having an average diameter of between 1 μm and 1000 μm. In some embodiments, the average diameter of the microparticles is between 200 μm and 800 μm. In some embodiments, the average diameter of the microparticles is between 400 μm and 600 μm. In some embodiments, a microparticle has an average diameter of about 1 μm, about 100 μm, about 200 μm, about 300 μm, about 400 μm, about 500 μm, about 600 μm, about 700 μm, about 800 μm, about 900 μm, or about 1000 μm. In some embodiment, the matrix comprises a mixture of two or more different sized microparticles. For example, in some embodiments, the matrix may comprise microparticles having an average diameter of about 1 μm and microparticles having an average diameter of between 500 μm and 600 μm. In some embodiments, spaces exist between the microparticles of the matrix. In some embodiments, the spaces have a maximum diameter of up to 500 μm. In some embodiments, the spaces have a maximum diameter of up to 250 μm. In some embodiments, the spaces have a maximum diameter of up to 125 μm. In some embodiments, the spaces have a maximum diameter of up to 50 μm. In some embodiments, the matrix may comprise particles, beads, or spheres having an average diameter of greater than 1 mm.

As used herein, the term "column" refers to a structure or apparatus that houses the matrix. The column can be any shape or size suitable to hold the matrix. In some embodiments, the column is a syringe. In some embodiments, the column comprises an inlet and an outlet. An inlet is a point of entrance for samples, solutions, buffers, or reagents into the column. An inlet can be an opening to the column, or can be an opening in a conduit that leads, directly or indirectly, to the column. An outlet is the opening at which sample, sample components, or reagents exit a column. The sample components and reagents that leave a chamber can be waste, i.e., sample components that are not to be used further, or can be sample components or reagents to be recovered, such as, for example, reusable reagents or target cells to be further analyzed or manipulated. An outlet can be an opening of the column approximate to a collection vessel, or an opening in a conduit that, directly or indirectly, leads from the column to the collection vessel. In some embodiments, the column may be connected to an automated system that controls the flow of cells and other reagents through the column and out of the column into one or more collection vessels. The column may include additional components, such as a mesh or filter, that prevent matrix loss from the outlet or clogging of the outlet.

As used herein, the term "functionalization" refers to any process that modifies a material by introducing a physical, chemical, or biological characteristic that is different from the characteristic originally found on the material. Generally, functionalization involves introducing functional groups into/onto the material. As used herein, a functional group is a particular group of atoms within a molecule that is responsible for the characteristic chemical reactions of those molecules. As used herein, a functional group may be positively or negatively charged. In some embodiments, a positively charged functional group may include amine, aldehyde, polyethylenimine (PEI), and/or guanidine groups. In some embodiments, functionalization may include a coupling agent to attach the group to the microparticle.

As used herein, the term "sample" refers to a biological sample. In some embodiments, the term sample refers to clinical samples obtained from a patient. In embodiments, a sample is obtained from a biological source (i.e., a "biological sample"), such as tissue, bodily fluid, or microorganisms collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). In some embodiments, the sample may be a mixture of multiple different cell types or comprise a single cell type. In some embodiments, solid samples, such as tissue biopsies, may be prepared into fluid samples, for example by chemical, enzymatic, or physical dissociation of the cells. In some embodiments, the sample may be cultured cells or cell lines. In some embodiments disclosed herein, the cell lines may be colon cancer cell lines such as SW620 cells; breast cancer cell lines, such as T47D cells; lung cancer cell lines, such as A549 cells; or acute lymphatic leukemia cell lines, such as CCRF-SB. In some embodiments, the cells may be white blood cells (WBCs) purified from a blood sample.

As used herein "cell surface charge" or "electrostatic charge" of a cell, refers to the net positive, negative, or neutral charge on the cell surface. It has recently been discovered that cancer cells are negatively charged on their cell surface. The disclosure described herein takes advantage of the net negative charge on the surface of cancer cells to isolate cancer cells from a biological sample.

As used herein, the terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer" includes premalignant, as well as malignant cancers. Examples of cancers may include blood, prostate, breast, colon, brain, lung, head & neck, ovarian, bladder, renal & testis, melanoma, liver, pancreatic and other gastrointestinal cancer. In some embodiments, the cancer may be in the form of circulating tumor cells (CTCs), i.e., tumor or cancer cells that circulates within the vasculature, lymphatic vessels, or other fluids. CTCs include, but are not limited to, leukemia cells or cells shed from a primary tumor.

As used herein, a "control" is an alternative sample used in an experiment for comparison purpose. A control can be "positive" or "negative." A "control cell sample" or "reference cell sample" as used herein, refers to cells from a control or reference sample. In certain embodiments, the reference or control cell sample is a wild type or a non-cancerous cell. In certain embodiments, the reference cell sample is purified or isolated (e.g., it is removed from its natural state). In other embodiments, the reference cell sample is from a non-tumor sample, e.g., a blood control, a normal adjacent tumor (NAT), or any other non-cancerous sample from the same or a different subject.

As used herein, the term "enrich" means increase the relative concentration of a sample component of a sample relative to other sample components (which can be the result of reducing the concentration of other sample components), or increase the absolute concentration of a sample component. For example, as used herein, "enriching" cancer cells from a sample includes increasing the proportion of cancer cells to all cells or other components in the sample, enriching cancer cells of a blood sample can mean increasing the concentration of cancer cells in the sample (for example, by reducing the sample volume) or reducing the concentration or number of other cellular components of the blood sample to increase the percentage of cells present that are cancer cells, and "enriching" cancer cells in a sample can mean increasing their concentration in the sample such as by reducing sample volume or reducing the number of 'non-cancer' cells in the sample.

As used herein, the term "isolation" refers to a process in which one or more components of a sample are spatially isolated from one or more other components of a sample. An isolation can be performed such that one or more sample components of interest is translocated to or retained in one or more areas of an isolation apparatus and at least some of the remaining components are translocated away from the area or areas where the one or more sample components of interest are translocated to and/or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. It is also possible to cause one or more sample components to be translocated to one or more areas and one or more sample components of interest or one or more components of a sample to be translocated to one or more other areas. Isolations can be achieved through, for example, filtration, or the use of physical, chemical, electrical, or magnetic forces. Non-limiting examples of forces that can be used in separations are electrostatic forces, gravity, mass flow, dielectrophoretic forces, traveling-wave dielectrophoretic forces, and electromagnetic forces.

As used herein, the term "capture" refers to a type of isolation in which one or more moieties or sample components is retained in or on one or more areas of a surface, chamber, chip, bead particles, tube, or any vessel that contains a sample, where the remainder of the sample can be removed from that area. For example, the isolation matrix described herein may be used to capture a cancer cell from a sample.

As used herein, the terms "subject" and "patient" refer to an organism that receives a diagnosis or treatment for a particular disease or condition. Examples of subjects and patients include mammals, such as humans, primates, pigs, goats, rabbits, hamsters, cats, dogs, guinea pigs, members of the Bovidae family (such as cattle, bison, buffalo, and yaks, among others), sheep, and horses, among others. A patient that may be diagnosed using the methods described herein may or may not be presenting symptoms of the disease. A patient that may be diagnosed using the methods described herein may have a genetic predisposition or lifestyle risk for the disease. For example, in some embodiments, the methods described herein may be used for early detection. A patient that may be diagnosed using the methods described herein may have previously recovered from the disease or be in remission. A patient that may be treated using the compositions and methods described herein may have an established disease, in which case the patient has been diagnosed as having the disease and has shown symptoms of the disease for a prolonged period of time (e.g., over the course of days, weeks, months, or years). Alternatively, a patient may be symptomatic for a particular disease, but has yet to be diagnosed with the disease by a physician. Other patients that may be treated using the compositions and methods described herein include those that have been diagnosed as having a disease or disorder, and may or may not be showing symptoms of the disease as of yet. Patients that may be treated using the compositions and methods described herein include those that have not been diagnosed as having a disease or disorder and may or may not have shown symptoms of the disease, but have a genetic predisposition or lifestyle risk for the disease.

As used herein, the terms "treat" or "treatment" refer to therapeutic treatment, in which the object is to inhibit or slow down (lessen) an undesired physiological change or disorder. Beneficial or desired clinical results of treatment include, without limitation, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already having the condition or disorder, as well as those prone to have the condition or disorder or those in which the condition or disorder is to be inhibited.

The present disclosure recognizes that screening, diagnosis, prognosis, and treatment of many conditions, including cancer, can depend on the detection, isolation, and enrichment of rare cells from a complex sample. Often, enrichment can be accomplished by one or more separation steps. In particular, the present disclosure recognizes that the enrichment or separation of rare cells including malignant cells from patient samples, such as the isolation of cancerous cells from patient body fluid samples, can aid in the detection and typing of such malignant cells and therefore aid in diagnostic decisions, as well as in the development of therapeutic modalities for patients.

Positively Charged Surfaces and Isolation Matrix

The present disclosure relies on the on the recent discovery that cancer cells are negatively charged on their cell surface. Accordingly, the present disclosure provides several positively charged surfaces, including but not limited to microparticles and capillary tubes, that were generated and tested for their ability to bind and capture cancer cells.

Microparticles described herein may be of any shape or size and made of any appropriate material. For example, the microparticles may comprise one or more of glass, nylon, hydrogel, ceramic, metal and/or any other suitable material. These microparticles may be of homogeneous material or coated with another material such as nickel. For example, in some embodiments, the microparticles are glass microspheres. In the embodiments, the microparticles are glass microspheres coated with nickel.

Capillary tubes described herein may be of any suitable volume, length, and diameter, and made of any appropriate material. For example, the capillary tubes may comprise one or more of glass, nylon, hydrogel, ceramic, metal and/or any other suitable material. These capillary tubes may be of homogeneous material or coated with another material such as nickel. In some embodiments, the capillary tubes are glass. In some embodiments, the capillary tubes are glass coated with nickel.

Other surfaces and substrates in addition to capillary tubes and microparticles (e.g., microspheres) may be utilized for the purposes of the present disclosure. For example, beads made of glass, nylon, hydrogel, ceramic, metal and/or any other suitable material and of a suitable size may be functionalized as disclosed herein to provide a positively charged surface capable of binding cancer cells. Other useful surfaces and substrates include, but are not limited to, beads, mesh, films, membranes, dishes, wells, epi tubes, blood collection tubes, bags (e.g., blood bags), beakers, microscope slides, microscope cover slips, microfluidic chambers, pipette tips, stirrers (e.g., magnetic stirrers), or any other surface or substrate through which a fluid same containing cancer cells can be passed or collected in.

Glass microspheres, capillary tubes, and other surfaces or substrates can be functionalized by the methods described herein to generate a positive charge on the surface of the microspheres or capillary tubes. For example, chemical or electrostatic reactions may be used to functionalize the surfaces with positively charged moieties such as amine, polyethylenimine (PEI), and/or guanidine groups. In some embodiments, the surfaces of the microparticles, capillary tubes, or other surfaces may be positively charged without being functionalized.

In some embodiments for example, amine coated surfaces may be prepared, such as amine coated glass beads or capillary tubes. For example, one or more glass beads may be used. In some embodiments, the glass beads may have a diameter of less than 1 mm, for example between 500 and 600 $\mu$m. In some embodiments, the glass beads may have a diameter of great than 1 mm, for example between 1.7 and 2.5 mm. In some embodiments, the glass beads are prepared by etching in 30% NaOH. The etched glass beads are washed 5 times with ddH20 to assure the removal of NaOH, and then washed again 3 times in ethanol to assure removal of ddH2O. The beads are then treated with 5% 3-Aminopropyltriethoxysilane solution by gently rotating for 2 h at room temperature. The beads are again washed 3 times with ethanol to assure the removal of the 3-Aminopropyltriethoxysilane solution, and then washed again 3 times in ddH2O to assure removal of ethanol. The beads are then frozen at −84° C., then freeze dried to remove water and to form the siloxane bonds. The same protocol can be used to coat the inside of the capillary tubes or surfaces of other devices such as coverslips, but instead of gently rotating, the capillary tube of device sits in the solution of 5% 3-Aminopropyltriethoxysilane for 2 hours while frequently moving the capillary tubes up and down to mix the solution.

In some embodiments, the amine coated surfaces may be prepared with a 10% 3-Aminopropyltriethoxysilane to generate 10% 3-Aminopropyltriethoxysilane coated surfaces. In some embodiments, the amine coated surfaces may be prepared with a 5% 3-Aminopropyltrimethoxysilane to generate 5% 3-Aminopropyltrimethoxysilane coated surfaces. In some embodiments, the amine coated surfaces may be prepared with a 10% 3-Aminopropyltrimethoxysilane to generate 10% 3-Aminopropyltrimethoxysilane coated surfaces.

In some embodiments, aldehyde coated surfaces may be prepared, such as aldehyde coated glass beads or capillary tubes. For example, one or more glass beads may be used. In some embodiments, the glass beads may have a diameter of less than 1 mm, for example between 500 and 600 μm. In some embodiments, the glass beads may have a diameter of great than 1 mm, for example between 1.7 and 2.5 mm. In some embodiments, the glass beads are prepared by etching in 30% NaOH. The etched glass beads are washed 5 times with ddH20 to assure the removal of NaOH, and then washed again 3 times in ethanol to assure removal of ddH2O. A solution of 5% silane coupling agent can be prepared by dissolving 2.5 ml of triethoxysilylbutyraldehyde in 50 ml of the 4% water in ethanol solution and rotating the solution in a plastic tube for 5 min at room temperature to allow hydrolysis and form reactive silanols. The beads are then treated with the 5% silane coupling agent solution by gently rotating for 2 h at room temperature. The beads are again washed 3 times with ethanol to assure the removal of the coupling agent, and then washed again 3 times in ddH2O to assure removal of ethanol. The beads are then frozen at −84° C., then freeze dried to remove water and to form the siloxane bonds. The same protocol can be used to coat the inside of the capillary tubes or surfaces of other devices such as coverslips, but instead of gently rotating, the capillary tube of device sits in the 5% silane coupling agent solution for 2 hours while frequently moving the capillary tubes up and down to mix the solution.

In some embodiments, polyethylenimine (PEI) coated surfaces may be prepared, such as PEI coated glass beads or capillary tubes. For example, one or more glass beads may be used. In some embodiments, the glass beads may have a diameter of less than 1 mm, for example between 500 and 600 μm. In some embodiments, the glass beads may have a diameter of great than 1 mm, for example between 1.7 and 2.5 mm. The PEI surfaces may be prepared at using a high pH or using a high-low pH reaction, or by using and electrostatic reaction.

For example, in embodiments, where a high pH reaction is used, an amine-containing protein solution can be prepared at a concentration of 10 mg/ml by dissolving 2.5 g of branched PEI in 50 ml of 0.1 M Sodium Borate, pH 9.5. Aldehyde coated beads, prepared as described above, are washed 3 times in PBS to neutralize the pH of the beads and 35 ml of the PEI solution and 350 μl of 5 M sodium cyanoborohydride in 1 N NaOH added to the beads and rotated at room temperature for 2 hrs. The beads are then washed 5 times in 30 ml PBS to assure removal of unreacted PEI.

In embodiments, where a high-low pH reaction is used, two solutions of amine-containing protein are prepared at a concentration of 10 mg/ml by dissolving 2.5 grams of branched Polyethylenimine (PEI) in 50 ml of each of 0.1 M Sodium Borate, pH 9.5, and 0.1 M sodium phosphate, 0.15 M NaCl, pH 7.2, to generate a high and low pH PEI solution, respectively. Aldehyde coated beads, prepared as described above, are washed 3 times in PBS to neutralize the pH of the beads. The beads are first resuspending in 35 ml of the high pH PEI solution and gently rotated for 15 min. The supernatant is then removed and the beads resuspended in 35 ml of the low pH PEI solution. 350 μl 5 M sodium cyanoborohydride in 1 N NaOH is then added to the beads, and they are rotated at room temperature for 2 hrs. The beads are then washed 5 times in 30 ml PBS to assure removal of unreacted PEI.

In embodiments, where an electrostatic reaction is used, the glass beads are prepared by etching in 30% NaOH. The etched glass beads are washed 5 times with ddH20 to assure the removal of NaOH, and then washed again 3 times in ethanol to assure removal of ddH20. An Aminoguanidine solution is prepared by dissolving 2 g of Aminoguanidine hydrochloride in 10 ml of DMSO. Once completely dissolved 40 ml of a MCF, pH 6.0 buffer is added to bring the total volume to 50 ml. 40 ml of the Aminoguanidine solution is then added to the washed beads and rotated for 2 h at room temperature. The beads are then washed 3 times with 30 ml of PBS to assure the removal of unreacted Aminoguanidine.

In some embodiments, histidine coated surfaces may be prepared, such as histidine coated glass beads or capillary tubes. For example, one or more glass beads may be used. In some embodiments, the glass beads may have a diameter of less than 1 mm, for example between 500 and 600 μm. In some embodiments, the glass beads may have a diameter of great than 1 mm, for example between 1.7 and 2.5 mm. A 5 mg/ml solution containing histidine is prepared by dissolving 25 mg of N-Acetyl-L-Histidine in 5 ml of MES buffer pH 6. A 0.5-0.1M EDC concentration solution is made by dissolving 250 mg of EDC in 5 ml of the N-Acetyl-L-Histidine in MES buffer solution made as above. 10% 3-Aminopropylmethoxysilane coated beads or any of the amine coated beads, prepared as described above, are rotated at room temperature with the EDC with N-Acetyl-L-Histidine in MES buffer for 2 hours to react. The beads are then washed 3 times with 30 ml of ddH20 to assure removal of unreacted solution. The same protocol can be used to coat the inside of the capillary tubes or surfaces of other devices such as coverslips, but instead of gently rotating, the capillary tube or device sits in the solution of the EDC with N-Acetyl-L-Histidine in MES buffer for 2 hours while frequently moving the capillary tube or device up and down to mix the solution.

For the purposes of the present disclosure, an isolation matrix can comprise a column or other suitable housing that is packed with positively charged microspheres or beads described herein. For example, a column can be packed with a plurality of microspheres (e.g., glass microspheres) or beads (e.g., glass beads) that have been functionalize such that the surface of the microparticles displays a positively charged moiety, such as one or more amine, polyethylenimine (PEI), and/or guanidine group. Similarly, an isolation matrix can comprise a single thin capillary tube, a plurality of capillary tubes, or other suitable tubes/chambers functionalized such that its inner surface is positively charged and of a diameter such that cells can be easily passed through the capillary tube or chamber making significant contact with its inner surface. Negatively charged CTCs can be bound to the functionalized inner surface by the positively charged moiety, such as one or more amine, polyethylenimine (PEI), and/or guanidine group.

In some embodiments, prior to applying the cells for isolation or capture on microparticle columns or capillary tubes, cells can be treated with positively charged nickel-coated micro or nano particles. These particles adhere to the negatively charged CTCs by simple electrostatic interaction resulting in CTCs decorated on the surface of these micro or nano nickel particles. In this embodiment, such decorated CTCs bind to the surface of glass microparticles, such as histidine coated glass microspheres, or the inner surface of capillary tubes, such as histidine coated capillary tubes, not by electrostatic interaction but by chelation between their nickel surface decoration and the imidazole group of a histidine moiety. A particular advantage of this embodiment is the ease of removal of such decorated cells from a microbead column or capillary tube by elution with imidazole, which breaks the chelation bond previously holding them in place. This allows for the captured cells to be more easily released from the column and used for additional downstream purposes, such as cancer diagnostics and other uses described herein.

Columns and Capillaries Containing an Isolation Matrix

Columns and capillaries can be prepared to contain the isolation matrix such that a biological sample is able to be passed through the matrix and the positively charged microparticles or capillaries capture and isolate the negatively charged cancer cells from the sample. The column or capillary may be any shape or size appropriate to contain the matrix and should include an input and output to allow the sample the enter and exit the column.

Figure 14:
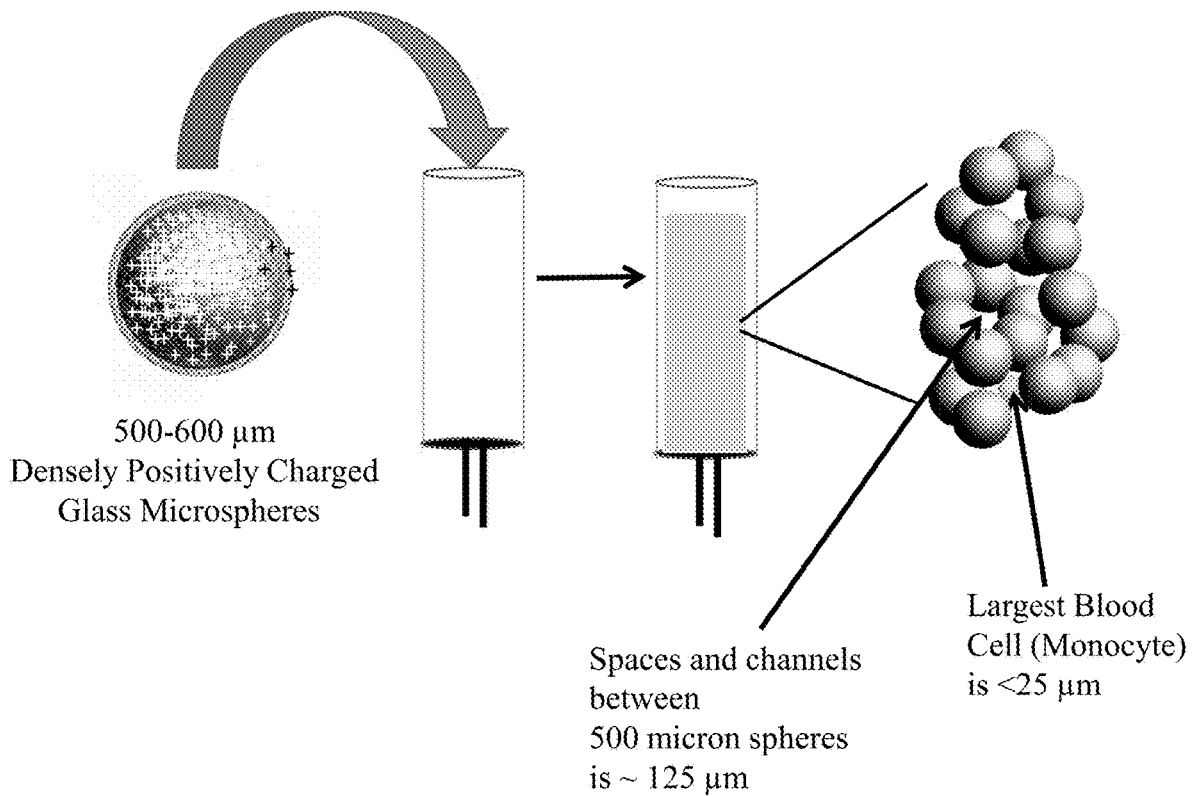
FIG. 14 shows an example of the column used in the embodiments described herein.

FIG. 14 depicts an exemplary workflow of preparing a column of the present disclosure. Once the microparticles have been deposited into the column, they will form a matrix, such that spaces exist between the microparticles that allow cells and other components of the sample to be filtered through the matrix.

Alternatively, cancer cells can be bound or isolated from a biological sample (e.g., blood) by contacting the biological sample with a positively charged surface as disclosed herein. Such surfaces can be prepared by functionalizing according to the methods disclosed herein.

Uses of Isolated Cancer Cells

Cancer cells captured using the methods and compositions described in the present disclosure can be used for multiple downstream purposes. The cancer cells may either be utilized directly in the column, still attached to the microparticles, the cancer cells may be lysed without elution from the column, the cancer cells may remain on the column, or the cancer cells may be eluted from the column and used for one or more downstream purposes, including but not limited to those described herein.

In some embodiments, the disclosed methods may be used to identify the presence of cancer cells in a blood sample from a subject for the purpose of diagnosing cancer, wherein the presence of cancer cells in a blood sample from said patient is indicative of the presence of a tumor in the body of said subject. The disclosed methods of detecting cancer or circulating tumor cells (CTC) allow for early detection of cancer before signs or symptoms of the cancer are otherwise apparent. As shown in the Examples provided herein, the disclosed methods and compositions are highly sensitive and able to isolate cancer cells/CTCs that are a vanishingly small portion of a sample. Accordingly, a previously unknown cancer could be detected in a subject by, for example, obtaining a blood sample from the subject and passing the blood sample through a positively charged matrix or surface disclosed herein. Any cells that bind to the matrix or surface are expected to be cancer cells and would be indicative of the subject having cancer or a tumor. In this way, early stage detection of previously unidentified cancer in a subject is possible. These methods are especially useful for detecting or diagnosing certain types of cancers that often otherwise evade detection until late stages, such as pancreatic and ovarian cancers.

Additionally or alternatively, the presence of cancer cells may be indicative of a likelihood of progression or metastasis of the tumor. In some embodiments, the present disclosure may be used to detect the presence of cancer in a patient that has already undergone treatment. For example, the present disclosure may be used to monitor remission/recurrence of cancer or detect minimal residual disease. In some embodiments, the cancer cells are isolated using the methods described herein, and the positive identification of the cancer cells is obtained by labeling said cells with one or more cancer marker-specific binders (e.g., antibodies). In some embodiments, the cancer cells are isolated using the methods described herein, and the positive identification of the cancer cells is obtained by detecting genetic signatures of cancer cells.

In some embodiments of the present disclosure, the type of cancer present in the sample may be unknown. Therefore, in some embodiments, the cancer cells are isolated using the methods described herein, and the cells visualized using fluorescent cell markers or colorometric markers to allow counting and/or determination of the presence of bound cancer cells. In some embodiments, the type of cancer cells may be identified following their isolation from a sample. Identification may be achieved, for example, using cancer-type specific biomarkers that may be bound by, e.g., fluorescent labels. The labeled cancer cells may be further analyzed using spectral imaging, fluorescence microscopy, visible light microscopy, or manual or auto mated image analysis. In some embodiments, the cancer cells may be genotyped to identify the cancer type. Unlike other present methods of identifying CTCs by specific tumor type biomarkers, the captured cells in this disclosure are defined as cancer cells simply by their negative surface charge. As such any cells bound too these described matrices are cancer cells and provide a positive diagnosis of cancer in patients from which the cells were derived. The type of cancer cell and its tissue of origin may be determined by tissue specific biomarkers which are not cancer specific.

In some embodiments, the disclosed compositions and methods may be used for monitoring of disease progression, response to therapy, or relapse/recurrence in a patient with cancer. In some embodiments, the number of cells captured using the methods described herein, are determined at different time intervals during the progression of the disease or during a treatment regimen lasting weeks, months or longer, or after a treatment regimen has been discontinued. An increase in the number of cancer cells over time is indicative of lack of response to therapy, relapse, higher risk of metastasis, worse prognosis, shortened projected survival time, or progression to a higher stage of cancer or growth rate of the tumor, or combinations of the above. A decrease or non-varying number of cancer cells is indicative of favorable response to therapy, stable status of the disease, or shrinkage of the tumor or remission or combinations of the above.

In some embodiments, the cancer cells isolated from a cancer patient may be characterized for their nucleic acid content. The RNA and/or DNA from the isolated cancer cells may be analyzed and the genetic content and/or gene expression pattern characterized in the cancer cells using one or more of the following methodologies: single nucleotide polymorphism analysis, quantitative PCR, RT-PCR, quantitative RT-PCR, FISH, DNA sequencing, multiplexed PCR, determination of the DNA methylation, total DNA content quantification, whole genome amplification (WGA), CGH, laser dissection microscopy (LDM), amplification from RNA, Oligonucleotide ligation assay (OLA), Chromosome immuno-precipitation (CHIP), southern blot, hybridization, amplification, ligation, enzymatic assays. DNA and/or RNA may be isolated from cancer cells bound to the matrices simply by lysis of these cells on the matrix and recovery of the lysate.

In some embodiments, the genetic content of the cancer cells is analyzed for the purpose of identifying the presence of mutations which can confer higher proliferation rates or chromosomal deletions spanning tumor suppressor genes or chromosomal amplification of tumor promoting genes. In some embodiments, the characterization of the genetic content of cancer cells isolated from a subject is used to tailor a personalized therapeutic course specific to said subject or to the particular cancer phenotype.

Some embodiments of the present disclosure may include the culturing and in vitro propagation of cancer cells isolated from a biological sample obtained from a cancer patient. In some embodiments, the patient-specific cultured cells may be used to evaluate progress in a clinical study of an experimental cancer therapy or drug candidate. The subjects in such trials may be human, but frequently they would include other mammals such as mice, rats, dogs, monkeys and the like. In this aspect, the method can be used to provide a clinical end point to measure the efficacy of an experimental cancer therapy or drug candidate that is faster and more quantitative than effectiveness, metastasis, or recurrence data alone. This provides a more rapid and quantitative assessment of the efficacy of the therapeutic being tested, and it provides additional information about how the therapeutic affects metastasis and recurrence probabilities for the cancer being treated. It thus provides more information about the overall effectiveness of the experimental therapy and reduces the time required for clinical trials.

In some embodiments, the cultured cancer cells obtained from a cancer patient blood sample are used to test in vitro the efficacy of candidate anti-cancer drugs or drug combinations before administration of the drug(s) to said patient, or before deciding whether to continue administration of the drug(s). In other embodiments, such cultured cancer cells are used to test new drug candidates or other experimental therapies as part of a clinical trial or even a primary screen for efficacy.

In some embodiments, the cancer cells isolated from a cancer patient using the methods of the present disclosure, are immortalized by in vitro culturing and selection which may or may not be aided by transfection of the cells with SV40 T-antigen or Telomerase or other suitable methods. The immortalized cells may then be used to test the efficacy of anticancer agents, screen for new anticancer agents, or any other investigation requiring immortalized cell lines.

In some embodiments, the cancer cells isolated from a cancer patient using the methods or compositions of the present disclosure may be used in invasiveness assays.

In some embodiments, the cancer cells isolated from a cancer patient may be used for the purpose of personalized immunotherapy, wherein proteins or nucleic acids or combinations thereof obtained from the cancer cells isolated from a cancer patient are incubated with WBC or a subfraction of WBC from said patient to stimulate a cancer specific immune response. The WBC or the subfraction of WBC exposed to the cancer cell tumor antigens are then re-inoculated into the patient.

In some embodiments, following the isolation of the cancer cells from a blood sample using the methods or compositions described herein, the cancer cells can be characterized using several immunoassays. For example, the cancer cells can be lysed, and the lysate centrifuged, and subjected to ELISA assay. In this case, specific protein of interest expressed in the cancer cells can be detected directly. This can provide a profile of the protein content in the cancer cells and allows the monitoring of how the cancer cell phenotype changes during the course of the disease or during the therapeutic treatment.

In some embodiments, the isolated cancer cells can be characterized by one or more functional or enzymatic assays. Telomerase activity has been identified in lung cancer cells as well as in cancer cells from many other cancers. Telomerase activity assay can be used to further characterize circulating tumor cells isolated with the depletion methods of the present disclosure or with positive selection methods well known to those skilled in the arts. In this case, telomerase repeat amplification protocol (TRAP) can be performed. Once the cancer cells are isolated, telomerase will be extracted using CHAPS based detergent buffer or any other suitable method. The supernatant of cell lysates will be used as template for telomerase extension reaction by PCR. Fluorescent PCR products are generated using fluorescently labeled primers, followed by capillary electrophoresis measurements. The larger the amount of fluorescent PCR product generated or the larger the length of the telomerase repeat amplification products, the higher the telomerase activity of the cancer cells in the sample, which can be an indicator of the aggressiveness of the tumor or of the number or fraction of cancer cells in the enriched sample.

In recent years antibody-based therapy has had significant success in the clinics and is now part of the standard arsenal used by clinicians to fight cancer. The methods of the present disclosure provide a unique approach in monitoring the effects and the efficacy of antibody-based therapies. In some embodiments the present disclosure can be used to detect the interaction between circulating cancer cells in the blood of a cancer patient and an immunotherapeutic such as a humanized exogenous antibody used for the therapy. Whether isolated cancer cells are bound to a therapeutic antibody can be determined by isolating a cancer cell and examining it for the presence of such antibodies.

In some embodiments, monitoring the interaction between therapeutic antibody and the cancer cells present in a blood sample can be used to evaluate the patient's response to therapy, wherein when the fraction of cancer cells bound to an immunotherapeutic agent such as an antibody is above a predetermined value, or increases over time for measurements at different time points, the outcome of the treatment is predicted to be favorable, and when the fraction of cancer cells bound to the antibody is below a predetermined value, or decreases over time for measurements at different time points, the outcome of the treatment is predicted to be unfavorable.

In some embodiments, cancer cells isolated using the disclosed methods or compositions can be used to prepare a patient-specific cancer vaccine. For example, the cancer cells may be lysed and packed into a vaccine particle, such as a yeast-cell wall particle (YCWP), that can be administered to the patient to stimulate the patient's immune system to attack the cancer. In some embodiments, the YCWP is capped. In some embodiments, the YWPC is capped with silicate. In some embodiments, the silicate comprises tetra-ethylorthosilicate, tetramethlorthosilicate, tetrapropylortho-silicate, or tetrabutylorthosilicate. In some embodiments, the YCWP is uncapped. YCWPs that are suitable for encapsulating a cancer cell lysate are known in the art and described in, for example, PCT/US2013/063091 (WO2014/040089).

The disclosed methods of isolating or capturing cancer cells and CTCs can be further used as a treatment by virtue of removal of cells from the patient. Surgical resection of a solid tumor is often the first-line of treatment for many forms of cancer, but no such option was available to date for hematological cancers. The disclosed methods of isolating or capturing cancer cells/CTCs can be used a treatment for hematological cancers, such as leukemias and lymphomas. Similarly, the disclosed methods of isolating or capturing cancer cells/CTCs can be used to treat, prevent, or minimize the risk of metastasis of other forms of cancer (e.g., solid tumors) by removing from circulation CTCs and cancer cells that could potentially invade tissues outside the primary tissue of origin of a given cancer. Thus, in some embodiments, the methods described herein can be used to remove cancer cells from the blood of a cancer patient and return the blood to the patient. For example, the blood of hematological cancer patients may be "filtered," and the cancer cells captured by an isolation matrix described herein. Following cancer cell removal, the blood may be returned to the patient. This process may be repeated until the patient is cancer free or that a significant debulking of the circulating cancer cells has occurred. Cancers that are suitable for treatment according to these methods include, but are not limited to, any hematological cancer, such as leukemias and lymphomas. Such treatments can utilize existing apheresis or dialysis technologies to pass the blood of a subject through a matrix or substrate comprising a positively charged surface as disclosed herein, thereby allowing CTCs to contact and bind to the charged surface or matrix.

Compositions and Kits

Also included herein are kits for functionalizing microparticles or surfaces, preparing isolation matrices, and/ or preparing columns for isolating cancer cells. In some embodiments, the kit may include unfunctionalized microparticles or surfaces, and reagents for functionalizing said microparticles or surfaces. The kit may include one or more already functionalized and/or positively charged microparticles or surfaces. In some embodiments, the kit may include reagents and apparatus for preparing the matrix, such as buffers, tubes and other required apparatus. In some embodiments, the kit may include components for preparing the column, for example syringes, buffers, and tubes.

In some embodiments, kits described herein may additionally or alternatively include reagents and apparatus used for downstream processing or analysis of the captured cancer cells. For example, the kits may include reagents or apparatus for culturing the isolated cells, identifying the isolated cells using cancer cell biomarkers, or extracting and analyzing nucleic acids from the captured cancer cells.

The kit may further comprise one or more of: wash buffers and/or reagents, hybridization buffers and/or reagents, labeling buffers and/or reagents, and detection means. The buffers and/or reagents are usually optimized for the amplification/ detection technique for which the kit is intended. Protocols for using these buffers and reagents for performing different steps of the procedure may also be included in the kit.

The present disclosure further provide columns for use in the disclosed methods. The column may comprise a plurality of beads or microparticles that comprise a positively charged surface, e.g., as a result of functionalization with a positively charged moiety, such as one or more amine, polyethylenimine (PEI), and/or guanidine group. Alternatively, the present disclosure provides capillary tubes that comprise a positively charged surface, e.g., as a result of functionalization with a positively charged moiety, such as one or more amine, polyethylenimine (PEI), and/or guanidine group.

Examples of Embodiments

Embodiment 1. A method of removing cancer cells from a biological sample, comprising: a) passing a biological sample comprising cancer cells through an isolation matrix comprising functionalized microspheres; and b) collecting the biological sample that flows through the isolation matrix in a first aliquot, wherein the cancer cells bind to the isolation matrix.

Embodiment 2. The method of embodiment 1, wherein the functionalized microspheres are functionalized with a positively charged function group.

Embodiment 3. The method of embodiment 1 or 2, wherein the functionalized microspheres are functionalized with amine, polyethylenimine (PEI), and/or guanidine groups.

Embodiment 4. The method of any one of embodiments 1-3, wherein the microspheres comprise glass, polymer, or resin.

Embodiment 5. The method of any one of embodiments 1-4, wherein the microspheres are between 500 μm and 600 μm in diameter.

Embodiment 6. The method of any one of embodiments 1-5, wherein the biological sample comprises blood.

Embodiment 7. The method of any one of embodiments 1-6, wherein the biological sample is obtained from a subject that has or is suspected of having cancer.

Embodiment 8. The method of embodiment 7, wherein the cancer is a hematological cancer or comprises a solid tumor.

Embodiment 9. The method of any one of embodiments 1-8, further comprising eluting the cancer cells bound to the isolation matrix into a second aliquot.

Embodiment 10. The method of any one of embodiments 7-9, wherein the first aliquot is administered back into the subject.

Embodiment 11. The method of any one of embodiments 1-9, further comprising detecting the presence or absence of a cancer cell in the biological sample.

Embodiment 12. The method of any of embodiments 7-11, further comprising lysing the cancer cells to obtain a cancer cell lysate.

Embodiment 13. The method of embodiment 12, further comprising incorporating the cancer cell lysate into a cancer vaccine.

Embodiment 14. The method of embodiment 12, further comprising determining the mRNA copy number from the cancer cell lysate.

Embodiment 15. The method of embodiment 14, wherein the mRNA copy number is determined by quantitative RT-PCR.

Embodiment 16. The method of any one of embodiments 1-15, further comprising calculating the number of cancer cells bound to the functionalized microspheres.

Embodiment 17. A cancer vaccine, prepared by a process comprising: a) contacting a biological sample comprising cancer cells with a positively charged surface, wherein the cancer cells bind to the positively charged surface; b) lysing the cancer cells to obtain a cancer cell lysate; and c) incorporating the cancer cell lysate into a yeast cell wall particle (YCWP).

Embodiment 18. A cancer vaccine comprising: a) a yeast cell wall particle (YCWP), and b) the cancer cell lysate of embodiment 12.

Embodiment 19. The vaccine of embodiment 17 or 18, wherein the YCWP is modified by capping with a silicate.

Embodiment 20. The vaccine of embodiment 19, wherein the silicate is selected from the group comprising tetraethylorthosilicate, tetramethlorthosilicate, tetrapropylorthosilicate, and tetrabutylorthosilicate.

Embodiment 21. The vaccine of any of embodiments 17-20, further comprising one or more adjuvants, excipients and preservatives.

Embodiment 22. A method for delivering a vaccine to a subject comprising administering to the subject the vaccine according to of any one of embodiments 17-21.

Embodiment 23. A method of treating or preventing cancer, comprising administering the vaccine of any of embodiments 17-21 to a subject in need thereof.

Embodiment 24. The method of embodiment 22 or 23, wherein the vaccine is administered subcutaneously, orally, or intravenously.

Embodiment 25. The method of embodiment 22 or 23, wherein the vaccine is administered to the dermis of the subject.

Embodiment 26. A method of treating cancer in a patient, comprising extracting cancer cells from the patient's blood by passing the blood through an isolation matrix comprising functionalized microspheres that bind to cancer cells.

Embodiment 27. The method of embodiment 26, wherein the functionalized microspheres are functionalized with a positively charged function group.

Embodiment 28. The method of embodiment 26 or 27, wherein the functionalized microspheres are functionalized with amine, polyethylenimine (PEI), and/or guanidine groups.

Embodiment 29. The method of any one of embodiments 26-28, wherein the microspheres comprise glass, polymer, or resin.

Embodiment 30. The method of any one of embodiments 26-29, wherein the microspheres are between 500 μm and 600 μm in diameter.

Embodiment 31. The method of any one of embodiments 26-30, wherein the patient has a hematological cancer or a malignant cancer.

Embodiment 32. The method of any one of embodiments 26-31, further comprising eluting the bound cancer cells from the isolation matrix.

Embodiment 33. The method of embodiment 32, further comprising lysing the eluted cells to obtain a lysate and incorporating the lysate into a cancer vaccine for treating the patient.

Embodiment 34. A method of detecting a cancer cell in a patient, comprising: a) passing a biological sample from the patient through an isolation matrix of functionalized microspheres, wherein the functionalized microspheres bind cancer cells; b) eluting the cancer cells from the matrix; and c) detecting the presence or absence of a cancer cell in the biological sample.

Embodiment 35. The method of embodiment 34, wherein the patient has a hematological cancer or a malignant cancer.

Embodiment 36. The method of embodiment 34 or 35, wherein the functionalized microspheres are functionalized with amine, polyethylenimine (PEI), and/or guanidine groups.

Embodiment 37. The method of any one of embodiments 34-36, wherein the microspheres comprise glass, polymer, or resin.

Embodiment 38. The method of any one of embodiments 34-37, wherein the microspheres are between 500 μm and 600 μm in diameter.

Embodiment 39. A cancer cell isolation matrix comprising functionalized microspheres comprising a positively charged function group, wherein the functionalized microspheres bind cancer cells.

Embodiment 40. The cancer cell isolation matrix of embodiment 39, wherein the functionalized microspheres are functionalized with amine, polyethylenimine (PEI), and/or guanidine groups.

Embodiment 41. The cancer cell isolation matrix of embodiment 39 or 40, wherein the microspheres comprise glass, polymer, or resin.

Embodiment 42. The cancer cell isolation matrix of any one of embodiments 39-41, wherein the microspheres are between 500 μm and 600 μm in diameter.

Embodiment 43. A kit for purifying cancer cells from a biological sample, comprising functionalized microspheres, wherein the functionalized microspheres bind cancer cells from the biological sample.

Embodiment 44. A method of preparing a column for cancer cell isolation, comprising: a) preparing an isolation matrix, wherein the isolation matrix comprises functionalized microspheres; and b) depositing the isolation matrix into a container with, wherein the container has an inlet and outlet.

Embodiment 45. The method of embodiment 44, wherein the functionalized microspheres are functionalized with a positively charged function group.

Embodiment 46. The method of embodiment 44 or 45, wherein the functionalized microspheres are functionalized with amine, polyethylenimine (PEI), and/or guanidine groups.

Embodiment 47. The method of any one of embodiments 44-46, wherein the microspheres comprise glass, polymer, or resin.

Embodiment 48. The method of any one of embodiments 44-47, wherein the microspheres are between 500 μm and 600 μm in diameter.

Embodiment 49. The method of any of embodiments 44-48, wherein preparing the functionalized microspheres comprises coating the microspheres with 5% 3-Aminopropyltriethoxysilane solution.

Embodiment 50. The method of any of embodiments 44-49, wherein preparing the functionalized microspheres comprises coating the microspheres with a 5% silane coupling agent.

Embodiment 51. The method of any of embodiments 44-50, wherein preparing the functionalized microspheres comprises coating the microspheres with polyethylenimine (PEI).

Embodiment 52. The method of any of embodiments 44-50, wherein preparing the functionalized microspheres comprises coating the microspheres with aminoguanidine.

Embodiment 53. The method of any of embodiments 44-51, wherein depositing the isolation matrix comprises depositing between 0.1 and 1 ml of functionalized microspheres into the container.

Embodiment 54. A method of removing cancer cells from a biological sample, comprising: a) passing a biological sample comprising cancer cells through a functionalized capillary tube; and b) collecting the biological sample that flows through the capillary tube in a first aliquot, wherein the cancer cells bind to the capillary tube.

Embodiment 55. The method of embodiment 54, wherein the capillary tube is functionalized with amine, polyethylenimine (PEI), and/or guanidine groups.

Embodiment 56. A method of removing cancer cells from a biological sample, comprising contacting a biological sample comprising cancer cells with a positively charged surface, wherein the cancer cells bind to the positively charged surface.

Embodiment 57. The method of embodiment 56, wherein the positively charged surface comprises functionalized with amine, polyethylenimine (PEI), and/or guanidine groups.

Embodiment 58. The method of embodiment 56 or 57, wherein the positively charged surface is made of glass, polymer, or resin.

Embodiment 59. The method of any one of embodiments 56-58, wherein the positively charged surface is selected from a bead, a microparticle, a capillary tube, a blood collection tube, a microscope slide, and a microscope slide cover.

Embodiment 60. The method of any one of embodiments 56-59, wherein the biological sample comprises blood.

Embodiment 61. The method of any one of embodiments 56-60, wherein the biological sample is obtained from a subject that has or is suspected of having cancer.

Embodiment 62. The method of embodiment 61, wherein the cancer is a hematological cancer or comprises a solid tumor.

Embodiment 63. The method of any one of embodiments 56-62, further comprising detecting the presence or absence of a cancer cell in the biological sample.

Embodiment 64. The method of any of embodiments 56-62, further comprising lysing the cancer cells to obtain a cancer cell lysate.

Embodiment 65. The method of embodiment 64, further comprising incorporating the cancer cell lysate into a cancer vaccine.

Embodiment 66. The method of any one of embodiments 56-65, further comprising calculating the number of cancer cells bound to the positively charged surface.

Embodiment 67. A cancer vaccine comprising: a) a yeast cell wall particle (YCWP), and b) the cancer cell lysate of embodiment 64.

Embodiment 68. The vaccine of embodiment 67, wherein the YCWP is modified by capping with a silicate optionally selected from tetraethylorthosilicate, tetramethlorthosilicate, tetrapropylorthosilicate, and tetrabutylorthosilicate.

Embodiment 69. The vaccine of embodiment 67 or 68, further comprising one or more adjuvants, excipients and preservatives.

Embodiment 70. A method for delivering a vaccine to a subject comprising administering to the subject the vaccine according to of any one of embodiments 67-69.

Embodiment 71. A method of treating or preventing cancer, comprising administering the vaccine of any of embodiments 67-69 to a subject in need thereof.

Embodiment 72. The method of embodiment 70 or 71, wherein the vaccine is administered subcutaneously, orally, or intravenously.

Embodiment 73. The method of embodiment 70 or 71, wherein the vaccine is administered to the dermis of the subject.

Embodiment 74. A method of treating cancer in a patient, comprising extracting cancer cells from the patient's blood by contacting the patient's blood with a positively charged surface, wherein the cancer cells bind to the positively charged surface, and returning the blood to the patient after contacting the positively charged surface.

Embodiment 75. The method of embodiment 75, wherein the positively charged surface comprises functionalized with amine, polyethylenimine (PEI), and/or guanidine groups.

Embodiment 76. The method of embodiment 74 or 75, wherein the positively charged surface is made of glass, polymer, or resin.

Embodiment 77. The method of any one of embodiments 74-76, wherein the positively charged surface is selected from a bead, a microparticle, a capillary tube, a blood collection tube, a microscope slide, and a microscope slide cover.

Embodiment 78. The method of any one of embodiments 74-77, wherein the patient has a hematological cancer or a malignant cancer.

Embodiment 79. A method of detecting a cancer cell in a subject, comprising removing cancer cells from a biological sample according to the method of any one of embodiments 56-60, and detecting the presence or absence of a cancer cell in the biological sample.

Embodiment 80. The method of embodiment 79, wherein the patient has a hematological cancer, a cancer comprising a solid tumor, or a malignant cancer.

Embodiment 81. A device for isolating cancer cells, comprising a positively charged surface that is comprises amine groups, polyethylenimine (PEI), guanidine groups, or any combination thereof.

Embodiment 82. The device of embodiment 81, wherein the positively charged surface is made of glass, polymer, or resin.

Embodiment 83. The device of embodiment 81 or 82, wherein the positively charged surface is selected from a bead, a microparticle, a capillary tube, a blood collection tube, a microscope slide, and a microscope slide cover.

EXAMPLES

The following examples are put forth so as to provide those of ordinary skill in the art with a description of how the compositions and methods claimed herein can be performed, made, and evaluated, and are intended to be purely exemplary and are not intended to limit the scope of the present disclosure.

Methods: The Following Materials and Methods were Used in the Examples.

Microsphere Functionalization

Amine Coated Glass Beads

5% 3-Aminopropyltriethoxysilane Beads: 10 g of MO-SCI OL-GLO0191B5-2338 500-600 µm glass beads were weighed into a 50 ml tube. The beads were rotated for 1 h in 30 ml of a 30% NaOH solution, prepared by adding 10 ml of 1M NaOH to 20 ml of ddH20, to etch the beads. A 4% water in ethanol solution was prepared by mixing 4 ml of ddH20 in 96 ml of ethanol and adjusting the pH to 4.5-5.5 with acetic acid. A 50 ml solution of 5% 3-Aminopropyl-triethoxysilane was prepared by dissolving 2.5 ml of 3-Aminopropyltriethoxysilane in 50 ml of the 4% water in ethanol solution and rotating the solution in a plastic tube for 15 min at room temperature to allow hydrolysis and form reactive silanols. The etched glass beads were then washed 5 times with 30 ml ddH20 to assure the removal of NaOH. The beads were then washed 3 times in 30 ml of ethanol to assure removal of ddH2O. 35 ml of the 5% 3-Aminopropyltri-ethoxysilane solution was then used to react the beads by gently rotating for 2 h at room temperature. The beads were then washed 3 times with 30 ml of ethanol to assure the removal of the 3-Aminopropyltriethoxysilane solution, then washed 3 times in 30 ml of ddH2O to assure removal of ethanol. The beads were then frozen at −84° C., then freeze dried to remove water and form the siloxane bonds. The same protocol can be used to coat the inside of capillary tubes or surfaces of other devices, such as coverslips, but instead of gently rotating, the capillary tube or other device sits in the solution of 5% 3-Aminopropyltriethoxysilane for 2 hours while frequently moving the capillary tube or device up and down to mix the solution.

10% 3-Aminopropyltriethoxysilane Beads: The same protocol was used to make 10% 3-Aminopropyltriethoxysilane beads as was used to make 5% 3-Aminopropyltriethoxysilane Beads, described above, except 5 ml of 3-Aminopropyltriethoxysilane was dissolved in the 4% water in ethanol solution. All other steps were the same. The same protocol can be used to coat the inside of capillary tubes or surfaces of other devices, such as coverslips, but instead of gently rotating, the capillary tube or other device sits in the solution of 10% 3-Aminopropyltriethoxysilane for 2 hours while frequently moving the capillary tube or device up and down to mix the solution.

5% 3-Aminopropyltrimethoxysilane Beads: 10 g of MO-SCI OL-GLO0191B5-2338 500-600 μm glass beads were weighed into a 50 ml tube. The beads were rotated for 1 h in 30 ml of a 30% NaOH solution, prepared by adding 10 ml of 1M NaOH to 20 ml of ddH20, to etch the beads. A 50 ml solution of 5% 3-Aminopropyltrimethoxysilane was prepared by dissolving 2.5 ml of 3-Aminopropyltrimethoxysilane in 50 ml of methanol and rotating the solution in a plastic tube for 15 min at room temperature to allow hydrolysis and form reactive silanols. The etched glass beads were then washed 5 times with 30 ml ddH20 to assure the removal of NaOH. The beads were then washed 3 times in 30 ml of methanol to assure removal of ddH2O. 35 ml of the 5% 3-Aminopropyltrimethoxysilane solution was then used to react the beads by gently rotating for 2 h at room temperature. The beads were then washed 3 times with 30 ml of methanol to assure the removal of the 3-Aminopropyltrimethoxysilane solution, then washed 3 times in 30 ml of ddH2O to assure removal of methanol. The beads were then frozen at −84° C., then freeze dried to remove water and form the siloxane bonds. The same protocol can be used to coat the inside of capillary tubes or surfaces of other devices, such as coverslips, but instead of gently rotating, the capillary tube or devices sits in the solution of 5% 3-Aminopropyltrimethoxysilane for 2 hours while frequently moving the capillary tube or device up and down to mix the solution.

10% 3-Aminopropyltrimethoxysilane Beads: The same protocol was used to make 10% 3-Aminopropyltriethoxysilane beads as was used to make 5% 3-Aminopropyltrimethoxysilane Beads, described above, except 5 ml of 3-Aminopropyltrimethoxysilane was dissolved in methanol. All other steps were the same. The same protocol can be used to coat the inside of capillary tubes or surfaces of other devices, such as coverslips, but instead of gently rotating, the capillary tube or other device sits in the solution of 10% 3-Aminopropyltrimethoxysilane for 2 hours while frequently moving the capillary tube or device up and down to mix the solution.

Aldehyde Coated Glass Beads

Beads were coated in aldehydes using the silane coupling agent, triethoxysilylbutyraldehyde. First 10 g of MO-SCI OL-GLO0191B5-2338 500-600 μm glass beads were weighed into a 50 ml tube. The beads were rotated for 1 h in 30 ml of a 30% NaOH solution, prepared by adding 10 ml of 1M NaOH to 20 ml of ddH20, to etch the beads. A 4% water in ethanol solution was prepared by mixing 4 ml of ddH20 in 96 ml of ethanol and adjusting the pH to 4.5-5.5 with acetic acid. A 50 ml solution of 5% silane coupling agent was prepared by dissolving 2.5 ml of triethoxysilylbutyraldehyde in 50 ml of the 4% water in ethanol solution and rotating the solution in a plastic tube for 5 min at room temperature to allow hydrolysis and form reactive silanols. The etched glass beads were then washed 5 times with 30 ml ddH20 to assure the removal of NaOH. The beads were then washed 3 times in 30 ml of ethanol to assure removal of ddH2O. 35 ml of the 5% silane coupling agent solution was then used to react the beads by gently rotating for 2 h at room temperature. The beads were then washed 3 times with 30 ml of ethanol to assure the removal of the silane coupling agent solution, then washed 3 times in 30 ml of ddH2O to assure removal of ethanol. The beads were then frozen at −84° C., then freeze dried to remove water and form the siloxane bonds. The same protocol can be used to coat the inside of capillary tubes or surfaces of other devices, such as coverslips, but instead of gently rotating, the capillary tube or other device sits in the solution of the 5% silane coupling agent for 2 hours while frequently moving the capillary tube or device up and down to mix the solution.

Polyethylenimine (PEI) Coated Glass Beads

Prepared by chemical reaction (high pH): A solution of amine-containing protein was prepared at a concentration of 10 mg/ml by dissolving 2.5 g of branched PEI in 50 ml of 0.1 M Sodium Borate, pH 9.5. 10 g of the aldehyde coated beads, prepared as described above, were weighed out in a 50 ml tube, and washed 3 times in PBS to neutralize the pH of the beads. 35 ml of the PEI solution and 350 μl of 5 M sodium cyanoborohydride in 1 N NaOH was added to the beads and rotated at room temperature for 2 hrs. The beads were then washed 5 times in 30 ml PBS to assure removal of unreacted PEI.

Prepared by chemical reaction (high-low pH): Two solutions of amine-containing protein were prepared at a concentration of 10 mg/ml by dissolving 2.5 grams on branched Polyethylenimine (PEI) in 50 ml of each of 0.1 M Sodium Borate, pH 9.5, and 0.1 M sodium phosphate, 0.15 M NaCl, pH 7.2, to generate a high and low pH PEI solution, respectively. 10 g of the aldehyde coated beads, prepared as described above, were weighed out in a 50 ml tube, and washed 3 times in PBS to neutralize the pH of the beads. The beads were first resuspending in 35 ml of the high pH PEI solution and gently rotated for 15 min. the supernatant was then removed and the beads resuspended in 35 ml of the low pH PEI solution. 350 μl 5 M sodium cyanoborohydride in 1 N NaOH was then added to the beads, and they were rotated at room temperature for 2 hrs. The beads were then washed 5 times in 30 ml PBS to assure removal of unreacted PEI.

Prepared by electrostatic reaction: 10 g of MO-SCI OL-GLO0191B5-2338 500-600 μm glass beads were weighed into a 50 ml tube. The beads were rotated for 1 h in 30 ml of a 30% NaOH solution, prepared by adding 10 ml of 1M NaOH to 20 ml of ddH20, to etch the beads. The beads were then washed 5 times with 30 ml ddH2O to assure the removal of NaOH and resuspended and rotated for 2 h at room temperature in 35 ml PEI solution prepared by dissolving 5 g of branched polyethyleneimine (PEI) in 35 ml of PBS. The beads were then washed 5 times in 30 ml PBS to assure removal of unreacted PEI.

Guanidine Coated Glass Beads

Prepared by electrostatic reaction: 10 g of MO-SCI OL-GLO0191B5-2338 500-600 μm glass beads were weighed into a 50 ml tube. The beads were rotated for 1 h in 30 ml of a 30% NaOH solution, prepared by adding 10 ml of 1M NaOH to 20 ml of ddH20, to etch the beads. The beads were then washed 5 times with 30 ml ddH2O to assure the removal of NaOH. An Aminoguanidine solution was then prepared by dissolving 2 g of Aminoguanidine hydrochloride in 10 ml of DMSO. Once completely dissolved 40 ml of a MCF, pH 6.0 buffer was added to bring the total volume to 50 ml. 40 ml of the Aminoguanidine solution was then added to the washed beads and rotated for 2 h at room temperature. The beads were then washed 3 times with 30 ml of PBS to assure the removal of unreacted Aminoguanidine.

Histidine Coated Glass Beads

Prepared by chemical reaction: A solution containing histidine was prepared at a concentration of 5 mg/ml by dissolving 25 mg of N-Acetyl-L-Histidine in 5 ml of MES buffer pH 6. A 0.5-0.1M EDC concentration solution was made by dissolving 250 mg of EDC in 5 ml of the N-Acetyl-L-Histidine in MES buffer solution made above. 10 g of the 10% 3-Aminopropylmethoxysilane coated beads, prepared as described above, were weighed out in a 50 ml tube. Alternatively any of the amine coated beads could be used. The EDC with N-Acetyl-L-Histidine in MES buffer was added to the tube with the amino beads and they were rotated at room temperature for 2 hours to react. Following the reaction time the beads were washed 3 times with 30 ml of ddH20 to assure removal of unreacted solution. The same protocol can be used to coat the inside of capillary tubes or surfaces of other devices, such as coverslips, but instead of gently rotating, the capillary tube or other device sits in the solution of the EDC with N-Acetyl-L-Histidine in MES buffer for 2 hours while frequently moving the capillary tube or device up and down to mix the solution.

Cell Culture

The cells were cultured in T75 or T25 flasks with cell culture media DMEM with 10% fetal bovine serum. The cells were incubated in a 37 C 5% CO2 incubator. The culture media was changed every 2-3 days and the cells were replated into new T75 or T25 flasks when the population got too big or when the cells were needed for experiments. All cell lines except CCRF-SB were attachment cell lines and too collect these cells the culture media was removed, the cell layer was briefly rinsed with PBS, then 1-2 ml of Trypsin-EDTA was added to the flasks causing the cells to disperse. The cells were then collected, and PBS was used to wash the flask once more and collect all extra cells. The cells were then centrifuged at 500×g for 5 min. The supernatant was discarded, and the cells were resuspended in a volume sufficient to perform a cell count with a hemocytometer. Based on the cell count between $1.0\times10^5$ and $1.0\times10^6$ cells were retained for further procedures described below and the rest of the cells were centrifuged at 500×g for 5 min and then resuspended in the culture media and replated in new flasks. CCRF-SB cell line was a suspension cell and to collect these cells a sufficient amount of culture media was removed; the cells were centrifuged at 500×g for 5 min. Then the supernatant was discarded, and the cells were resuspended in a volume sufficient to perform a cell count with a hemocytometer. Based on the cell count between $1.0\times10^5$ and $1.0\times10^6$ cells were retained for further procedures described below and the rest of the cells were centrifuged at 500×g for 5 min and then resuspended in the culture media and put in new flasks.

Red Blood Cell Lysis and Whole Blood Washing 5 ml of human whole blood was collected in a 15 ml centrifuge tube and washed with 5 ml PBS to remove any serum. The blood was then centrifuged at 500×g for 5 min and the supernatant removed. 5 ml ACK lysing buffer was added to the washed blood and allowed to incubate at room temperature for 7-10 min. 5 ml of PBS was then added and the sample centrifuged at 500×g for 5 min. The supernatant was removed and the pellet resuspended in 5 ml ACK lysing buffer and allowed to incubate for a further 7-10 min. 5 ml of PBS was then added and the sample again centrifuged at 500×g for 5 min. The lysis, incubation, centrifugation steps were repeated until the pellet was white. The pellet was then resuspended in 5 ml PBS. In some embodiments the human whole blood was simply washed to remove plasma and serum which has a negative charge and would interfere with the charged microparticles or capillary tubes. 5 ml of human whole blood was collected in a 15 ml centrifuge tube and washed with 5 ml PBS to remove any serum and/or plasma. The blood was then centrifuged at 500×g for 5 min and the supernatant removed. This washing step was performed 2 more times. The final washed blood was brought up to a volume of 5 ml with PBS and was ready for cells to be added for use on the microparticle column or capillary tubes as described in the present disclosure.

Cell Staining

Between $1.0\times10^5$ and $1.0\times10^6$ cells were collected from culture and resuspended in 1 ml of PBS. Cells were stained with 12 μl of a premade solution of 1 μl of calcein AM dye in 100 μl of DMSO and incubated in the dark on ice for 1-3 hrs. Cells were then centrifuged at 500×g for 5 min. The supernatant was discarded, and the cells washed in 1 ml PBS and centrifuged again at 500×g for 5 min. The supernatant was discarded, and the cells were resuspended in 1 ml of PBS.

Cells Mixed with Nickel-Coated Particles Prior to Isolation

In some moieties prior to applying the cells for isolation or capture on microparticle columns or single capillary tubes, cells are treated with positively charged nickel-coated micro or nano particles. Between $1.0\times10^5$ and $1.0\times10^6$ cells were collected from culture and resuspended in 1 ml of PBS. Cells were stained using the method above. 100 μl, approximately $1.0\times10^5$ stained cells, were added to a tube and 1-100 μl of Nickel-coated nano or microparticles were added to the cells such that there were approximately 100-1000 nickel particles per cell. The mixture was brought up to 500 ml with PBS and rotated for 15 min to allow the nickel particles to react with the cells. Following the incubation, the cells with nickel particle solution were ready to be used on the microparticle column or capillary tubes as described in the present disclosure.

Column Preparation

A column was prepared by placing a piece of 40 μm cell strainer mesh between a 1 ml syringe and a 23 gauge needle. The mesh was used to prevent the beads from getting stuck in the needle tip. Using a funnel the appropriate amount (e.g., 0.5 ml) of dry functionalized glass microspheres were added into an Eppendorf tube and the volume brought up to 1.5 ml with PBS. The tip was cut off a plastic transfer pipette and carefully the microparticles in PBS were pipetted into the column until they reached the 0.5 ml mark on the syringe. As many air bubbles and gaps between the beads were removed as possible. The column was washed 5 times with 500 μl of PBS to assure it is thoroughly washed. The column was allowed to run until it stopped dripping.

Capillary Tube Preparation and Procedure

The capillary tubes were prepared by treating it with different functional groups as described previously. A single capillary tube was used for each run. The cells were collected and stained as described previously. 100 μl, approximately $1.0\times10^5$ stained cells, were added to a tube ("Initial Cell Solution") and the volume brought up to 500 μl with 400 μl PBS. The cells were mixed thoroughly and added to a capillary tube by using a micropipette with a long tip to carefully pipette the cells down the inside of the capillary tube making sure the cell solution contacted the side of the capillary tube. The cells were added 100 μl at a time, making sure to avoid air bubbles, and the flow-through collected in a second tube ("Pass-Through"). Once the capillary tube stopped running, the capillary tube was washed with 500 µl PBS, added 100 µl at a time, making sure to avoid air bubbles, and the flow-through collected in a third tube ("First Wash"). Once the capillary tube had stopped running, the capillary tube was washed a second time with 500 µl PBS, added 100 µl at a time, making sure to avoid air bubbles, and the flow-through collected in a fourth tube ("Second Wash"). Once the capillary tube had stopped running, the capillary tube was analyzed under a microscope to see an adherence of green-fluorescing cells attached to the inner surface of the capillary tube.

Single Bead Diagnostics

In some embodiments, a single functionalized bead was used in the assays described herein. For example, a single bead functionalized as described above, and having a diameter large enough to be handled with forceps was used. The bead has a diameter of greater than 1 mm, or more specifically, between 1.7 mm and 2.5 mm. The bead was placed in a tube with a patient blood sample and rotated for 1 hour at room temperature. The bead was then removed from the tube, washed in PBS, and the cells lysed and used for downstream analysis, as described below.

Cancer Cell Lysis

The binding of tumor cells to the positively charged bead or matrices disclosed herein is unusually tight and the cells cannot be easily removed intact. Accordingly, tumor cell lysate was generated by exposing the matrices containing bound circulating tumor cells (CTC) to lysis conditions such as rapid freeze thaw or by chemical lysis for all diagnostic and therapeutic steps following tumor cell capture from patient blood.

Example 1. Isolation of Colon Cancer Cells

Approximately $1.0 \times 10^6$ SW620 colon cancer cells were stained using the method described above. 100 µl, approximately $1.0 \times 10^5$ stained cells, were added to a tube ("Initial Cell Solution") and the volume brought up to 500 µl with 400 µl PBS. The cells were mixed thoroughly and added to a column of 0.5 ml of either 5% 3-Aminopropyltriethoxysilane or 10% 3-Aminopropyltrimethoxysilane beads, prepared as explained above. The cells were added 100 µl at a time, making sure to avoid air bubbles, and the flow-through collected in a second tube ("Pass-Through"). Once the column had stopped dripping, the column was washed with 500 µl PBS, added 100 µl at a time, making sure to avoid air bubbles, and the flow-through collected in a third tube ("First Wash"). Once the column had stopped dripping, the column was washed a second time with 500 µl PBS, added 100 µl at a time, making sure to avoid air bubbles, and the flow-through collected in a fourth tube ("Second Wash"). Once the column had stopped dripping, the needle was capped and the cells from each of the four tubes were analyzed under a microscope.

Figure 1:
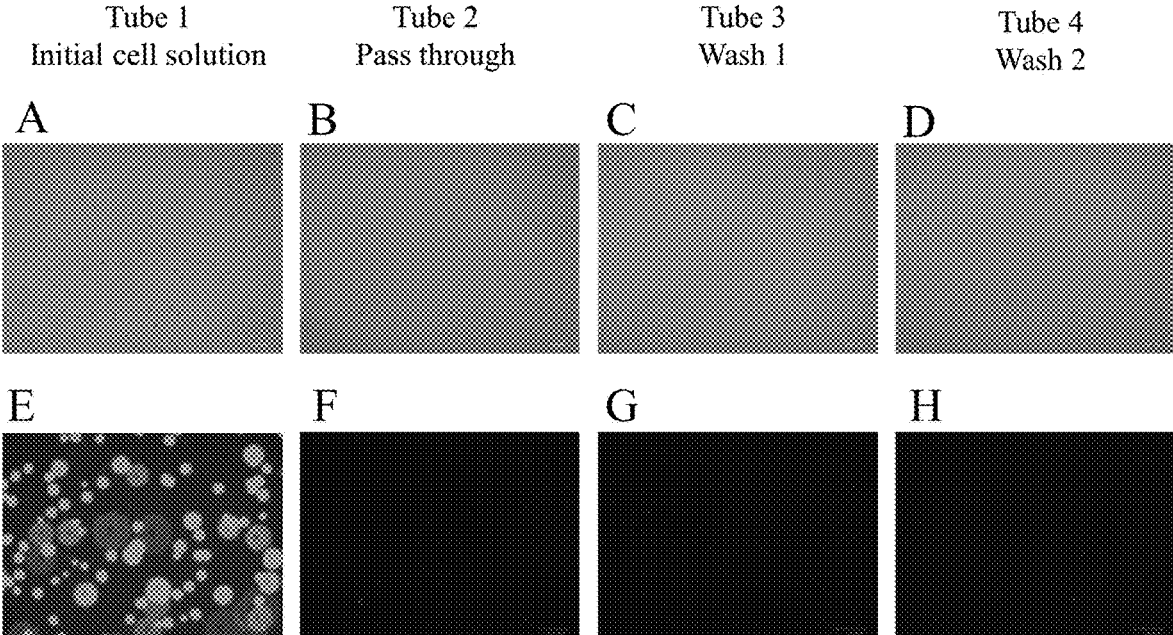
FIG. 1 shows bright field and GFP images of a SW620 colon cancer cell line before and after passing approximately $1.0 \times 10^5$ cells through a column prepared with 0.5 ml of 5% 3-Aminopropyltriethoxysilane Bead matrix (A-D). Colon cancer cells are seen under the green fluorescence view (E-H). All cancer cells were captured by the bead matrix as indicated by lack of stained cells in F-G.

FIG. 1 shows a bright field and green fluorescence view of 10 µl of each of the Initial Cell Solution (A and E), the Pass-Through sample (B and F), the First Wash sample (C and G), and the Second Wash sample (D and H) for the colon cancer cells passed through the 5% 3-Aminopropyltriethox-ysilane bead column. Viable colon cancer cells are visualized as green fluorescence when looked at under the microscope with green light due to calcein AM staining. Multiple cells can be seen in the Initial Cell Solution, however in each of the Pass-Through and First and Second Wash samples, no cells are seen, indicating the viable colon cancer cells remained in the column and were captured by the positively charged 5% 3-Aminopropyltriethoxysilane beads. The experiment was repeated with similar results.

Figure 2:
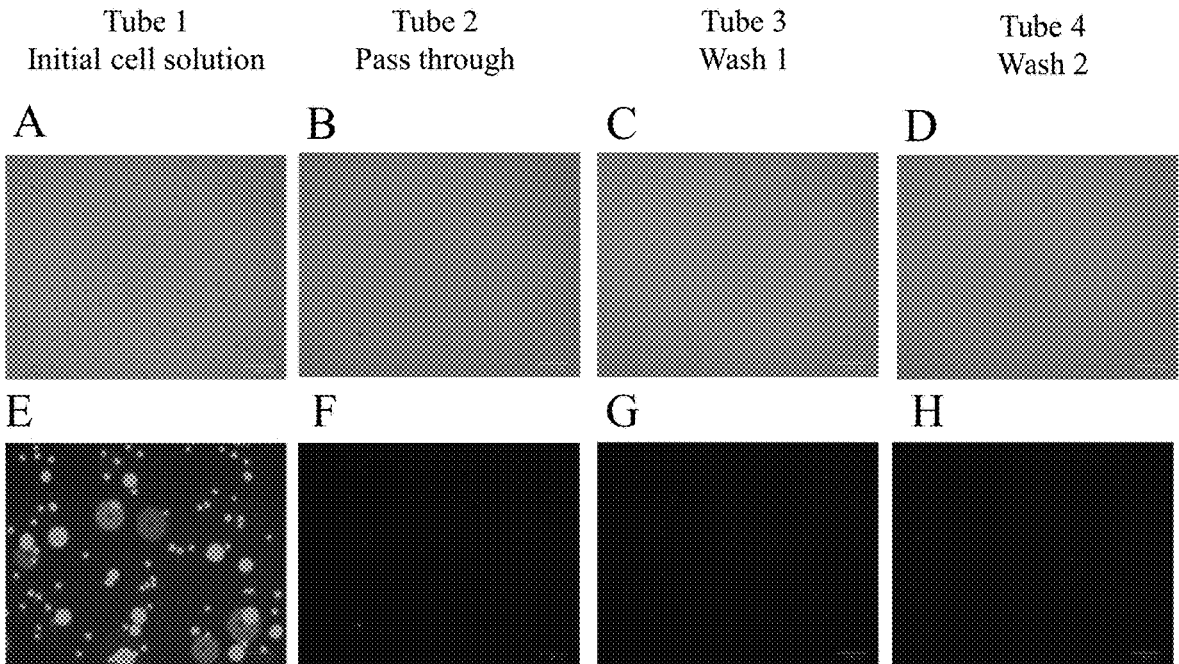
FIG. 2 shows bright field and GFP images of a SW620 colon cancer cell line before and after passing approximately $1.0 \times 10^5$ cells through a column prepared with 0.5 ml of 10% 3-Aminopropyltrimethoxysilane Bead matrix (A-D). Colon cancer cells are seen under the green fluorescence view (E-H). Most cancer cells were captured by the bead matrix as indicated by minimal number of stained cells in F-G

FIG. 2 shows a bright field and green fluorescence view of 10 µl of each of the Initial Cell Solution (A and E), the Pass-Through sample (B and F), the First Wash sample (C and G), and the Second Wash sample (D and H) for the colon cancer cells passed through the 10% 3-Aminopropylt-rimethoxysilane bead column. Viable colon cancer cells are visualized as green fluorescence when looked at under the microscope with green light due to calcein AM staining. Multiple cells can be seen in the Initial Cell Solution, however in each of the Pass-Through and First and Second Wash samples, no cells are seen, indicating the viable colon cancer cells remained in the column and were captured by the positively charged 10% 3-Aminopropyltriethoxysilane beads.

Each of the 5% 3-Aminopropyltriethoxysilane or 10% 3-Aminopropyltrimethoxysilane bead columns demonstrated similar results for capturing the colon cancer cells.

Example 2. Isolation of Breast Cancer Cells

Approximately $5.0 \times 10^5$ T47D cancer cells were stained using the method described above. 100 µl, approximately $1.0 \times 10^5$ stained cells, were added to a tube ("Initial Cell Solution") and the volume brought up to 500 µl with 400 µl PBS. The cells were mixed thoroughly and added to a column of 0.5 ml of either 5% 3-Aminopropyltriethoxysi-lane or 10% 3-Aminopropyltrimethoxysilane beads, prepared as explained above. The cells were added 100 µl at a time, making sure to avoid air bubbles, and the flow-through collected in a second tube ("Pass-Through"). Once the column had stopped dripping, the column was washed with 500 µl PBS, added 100 µl at a time, making sure to avoid air bubbles, and the flow-through collected in a third tube ("First Wash"). Once the column had stopped dripping, the column was washed a second time with 500 µl PBS, added 100 µl at a time, making sure to avoid air bubbles, and the flow-through collected in a fourth tube ("Second Wash"). Once the column had stopped dripping, the needle was capped and the cells from each of the four tubes were analyzed under a microscope.

Figure 3:
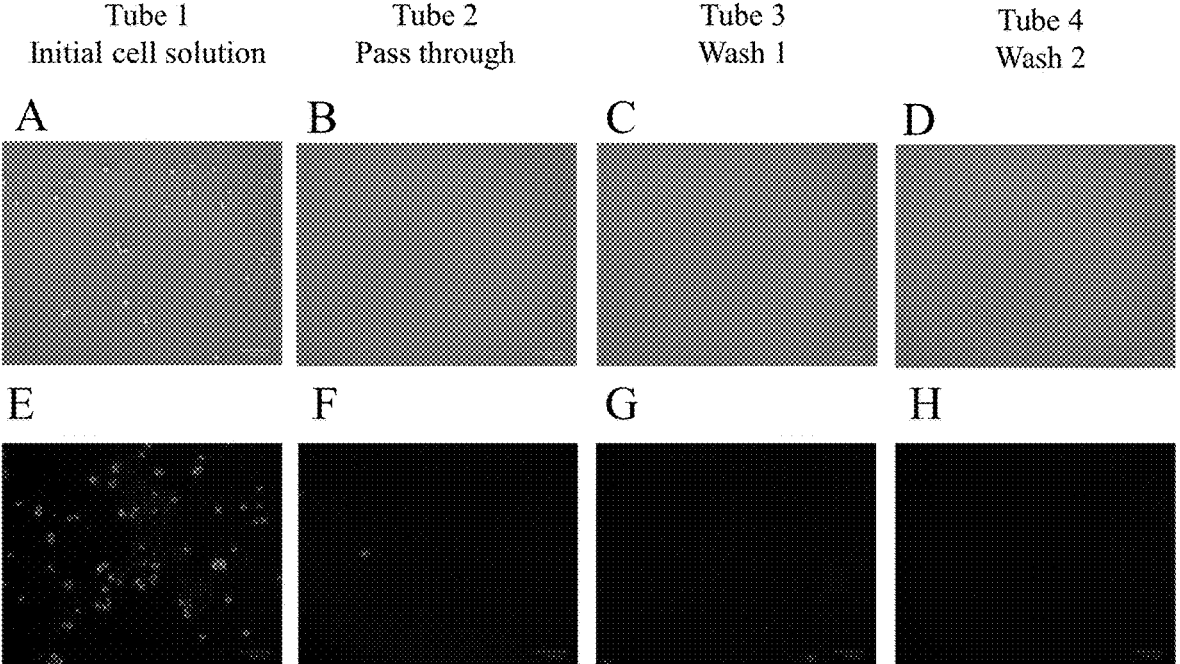
FIG. 3 shows bright field and GFP images of a T47D breast cancer cell line before and after passing approximately $1.0 \times 10^5$ cells through a column prepared with 0.5 ml of 5% 3-Aminopropyltriethoxysilane Bead matrix (A-D). Breast cancer cells are seen under the green fluorescence view (E-H). Most cancer cells were captured by the bead matrix as indicated by minimal number of stained cells in F-G

FIG. 3 shows a bright field and green fluorescence view of 10 µl of each of the Initial Cell Solution (A and E), the Pass-Through sample (B and F), the First Wash sample (C and G), and the Second Wash sample (D and H) for the breast cancer cells passed through the 5% 3-Aminopropyl-triethoxysilane bead column. Viable breast cancer cells are visualized as green fluorescence when looked at under the microscope with green light due to calcein AM staining. Multiple cells can be seen in the Initial Cell Solution, however minimal cells are seen in the Pass-Through sample, and no cells are seen in each of the First and Second Wash samples. This indicates that the viable breast cancer cells remained in the column and were captured by the positively charged 5% 3-Aminopropyltriethoxysilane beads.

Figure 4:
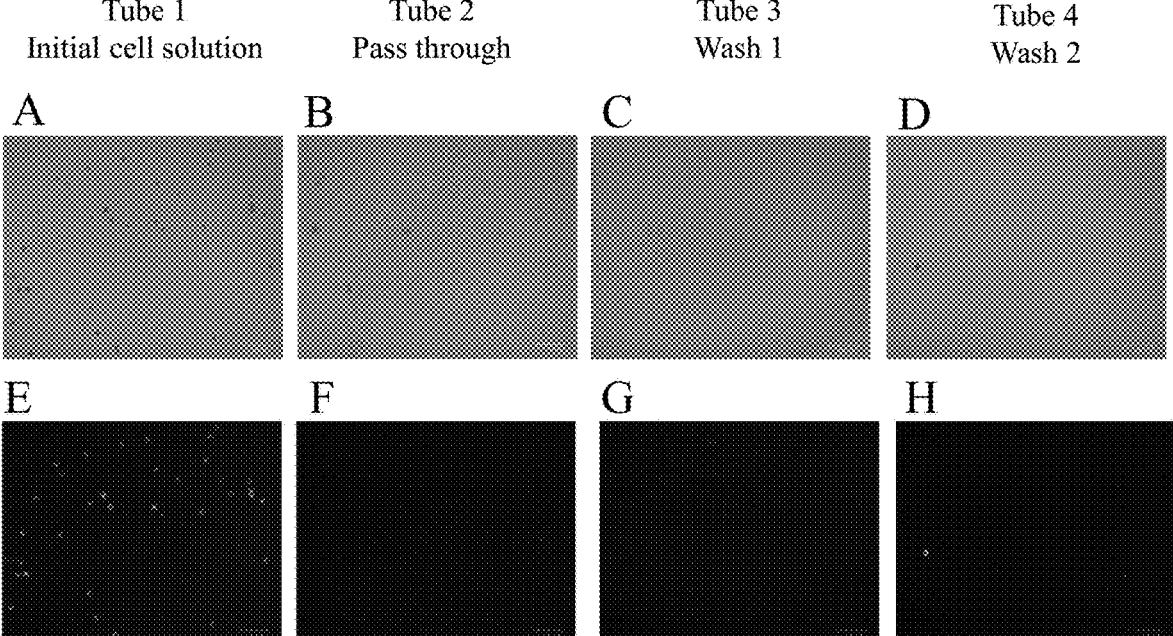
FIG. 4 shows bright field and GFP images of a T47D breast cancer cell line before and after passing approximately $1.0 \times 10^5$ cells through a column prepared with 0.5 ml of 10% 3-Aminopropyltrimethoxysilane Bead matrix (A-D). Breast cancer cells are seen under the green fluorescence view (E-H). Most cancer cells were captured by the bead matrix as indicated by minimal number of stained cells in F-G

FIG. 4 shows a bright field and green fluorescence view of 10 µl of each of the Initial Cell Solution (A and E), the Pass-Through sample (B and F), the First Wash sample (C and G), and the Second Wash sample (D and H) for the breast cancer cells passed through the 10% 3-Aminopropy-ltrimethoxysilane bead column. Viable breast cancer cells are visualized as green fluorescence when looked at under the microscope with green light due to calcein AM staining. Multiple cells can be seen in the Initial Cell Solution, however in each of the Pass-Through and First and Second Wash samples, minimal cells are seen, indicating the viable breast cancer cells remained in the column and were captured by the positively charged 10% 3-Aminopropyltrimethoxysilane beads.

Each of the 5% 3-Aminopropyltriethoxysilane or 10% 3-Aminopropyltrimethoxysilane bead columns demonstrated similar results for capturing the breast cancer cells.

Example 3. Isolation of Lung Cancer Cells

Approximately $1.0 \times 10^5$ A549 lung cancer cells were stained using the method described above. 100 µl, approximately $1.0 \times 10^5$ stained cells, were added to a tube ("Initial Cell Solution") and the volume brought up to 500 µl with 400 µl PBS. The cells were mixed thoroughly and added to a column of 0.5 ml of either 5% 3-Aminopropyltriethoxysilane or 10% 3-Aminopropyltrimethoxysilane beads, prepared as explained above. The cells were added 100 µl at a time, making sure to avoid air bubbles, and the flow-through collected in a second tube ("Pass-Through"). Once the column had stopped dripping, the column was washed with 500 µl PBS, added 100 µl at a time, making sure to avoid air bubbles, and the flow-through collected in a third tube ("First Wash"). Once the column had stopped dripping, the column was washed a second time with 500 µl PBS, added 100 µl at a time, making sure to avoid air bubbles, and the flow-through collected in a fourth tube ("Second Wash"). Once the column had stopped dripping, the needle was capped and the cells from each of the four tubes were analyzed under a microscope.

Figure 5:
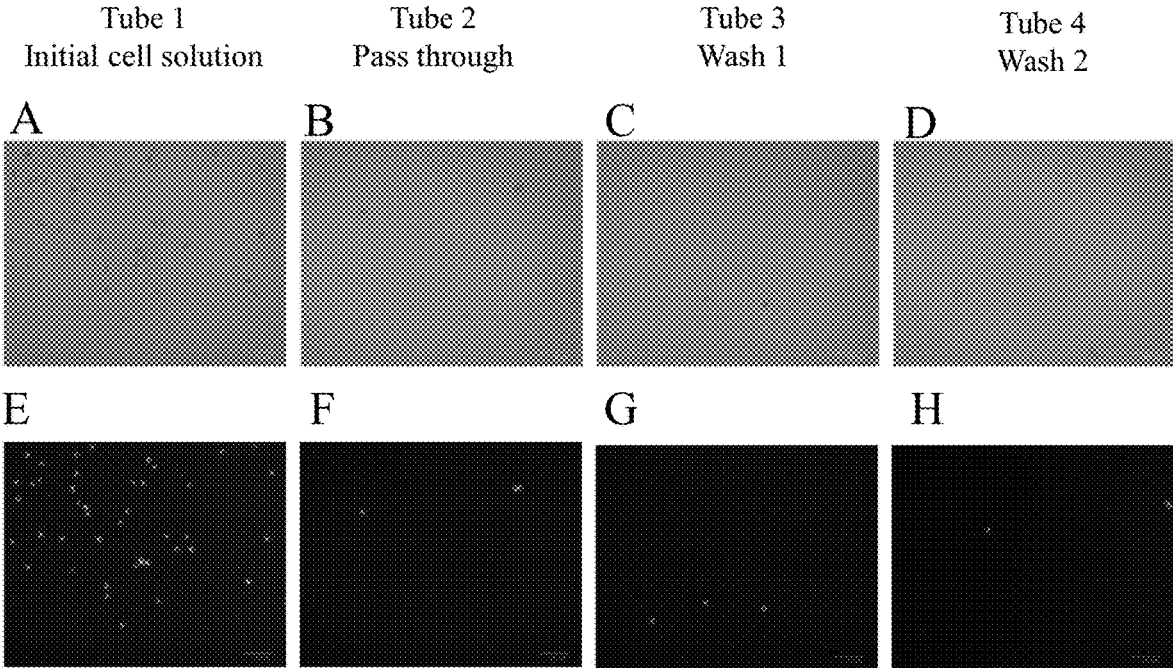
FIG. 5 shows bright field and GFP images of an A549 lung cancer cell line before and after passing approximately $1.0 \times 10^5$ cells through a column prepared with 0.5 ml of 5% 3-Aminopropyltriethoxysilane Bead matrix (A-D). Lung cancer cells are seen under the green fluorescence view (E-H). Most cancer cells were captured by the bead matrix as indicated by minimal number of stained cells in F-G.

FIG. 5 shows a bright field and green fluorescence view of 10 µl of each of the Initial Cell Solution (A and E), the Pass-Through sample (B and F), the First Wash sample (C and G), and the Second Wash sample (D and H) for the lung cancer cells passed through the 5% 3-Aminopropyltriethoxysilane bead column. Viable lung cancer cells are visualized as green fluorescence when looked at under the microscope with green light due to calcein AM staining. Multiple cells can be seen in the Initial Cell Solution, however minimal cells are seen in the Pass-Through, First and Second Wash samples. This indicates that the majority of the viable lung cancer cells remained in the column and were captured by the positively charged 5% 3-Aminopropyltriethoxysilane beads, however some cells were not captured. The experiment was repeated with similar results.

Figure 6:
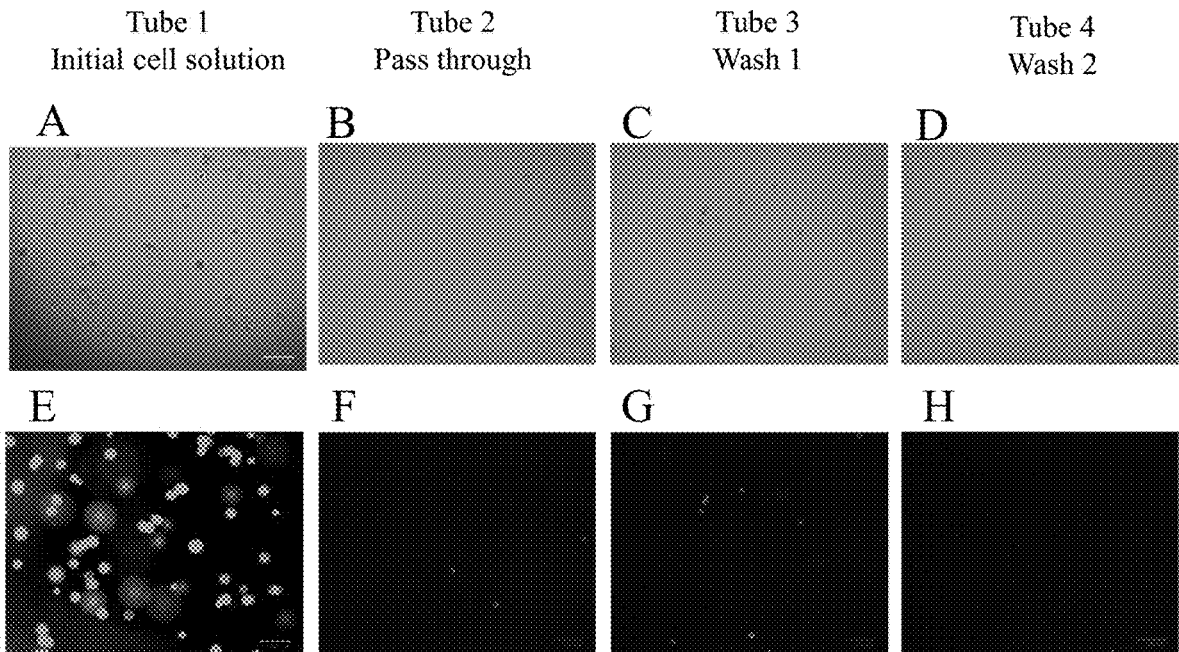
FIG. 6 shows bright field and GFP images of an A549 lung cancer cell line before and after passing approximately $1.0 \times 10^5$ cells through a column prepared with 0.5 ml of 10% 3-Aminopropyltrimethoxysilane Bead matrix (A-D). Lung cancer cells are seen under the green fluorescence view (E-H). Most cancer cells were captured by the bead matrix as indicated by minimal number of stained cells in F-G.

FIG. 6 shows a bright field and green fluorescence view of 10 µl of each of the Initial Cell Solution (A and E), the Pass-Through sample (B and F), the First Wash sample (C and G), and the Second Wash sample (D and H) for the lung cancer cells passed through the 10% 3-Aminopropyltrimethoxysilane bead column. Viable lung cancer cells are visualized as green fluorescence when looked at under the microscope with green light due to calcein AM staining. Multiple cells can be seen in the Initial Cell Solution, however minimal cells are seen in the Pass-Through, First and Second Wash samples. This indicates that the majority of the viable lung cancer cells remained in the column and were captured by the positively charged 10% 3-Aminopropyltrimethoxysilane beads, however some cells were not captured.

Each of the 5% 3-Aminopropyltriethoxysilane or 10% 3-Aminopropyltrimethoxysilane bead columns demonstrated similar results for capturing the lung cancer cells. However, since the number of cells that were not captured was more prominent than any of the other cell lines examined, the 5% 3-Aminopropyltriethoxysilane column was repeated once with more beads and the same number of cells, and once with the same number of beads and less cells.

These experiments were set up to see if this cell line requires a column with a higher capacity via bead increase.

Figure 7:
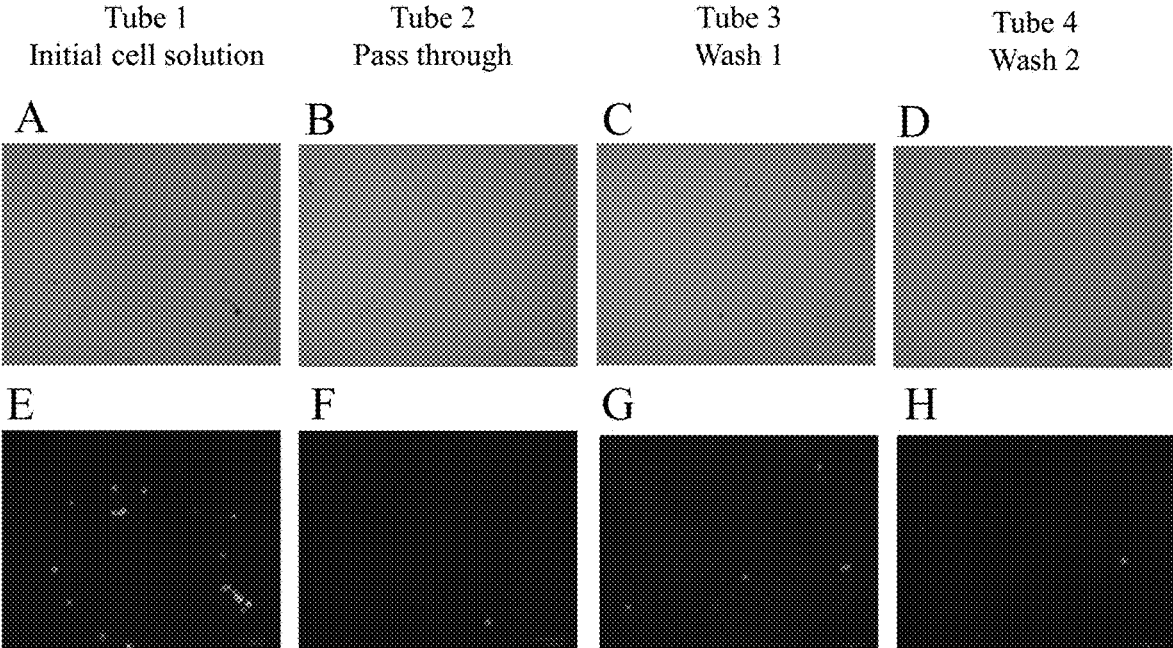
FIG. 7 shows bright field and GFP images of an A549 lung cancer cell line before and after passing approximately $1.0 \times 10^5$ cells through a column prepared with 0.8 ml of 5% 3-Aminopropyltriethoxysilane Bead matrix (A-D). Lung cancer cells are seen under the green fluorescence view (E-H). Most cancer cells were captured by the bead matrix as indicated by minimal number of stained cells in F-G.

For the experiment performed with more beads and the same number of cells, the experiment was performed identical to the described above, except the column was prepared with 0.8 ml of 5% 3-Aminopropyltriethoxysilane beads. Results can be seen in FIG. 7. Multiple cells can be seen in the Initial Cell Solution, however fewer cells are seen in the Pass-Through, First and Second Wash samples as compared to the 0.5 ml column. This indicates that this cell line may require a higher capacity to improve cell binding.

Figure 8:
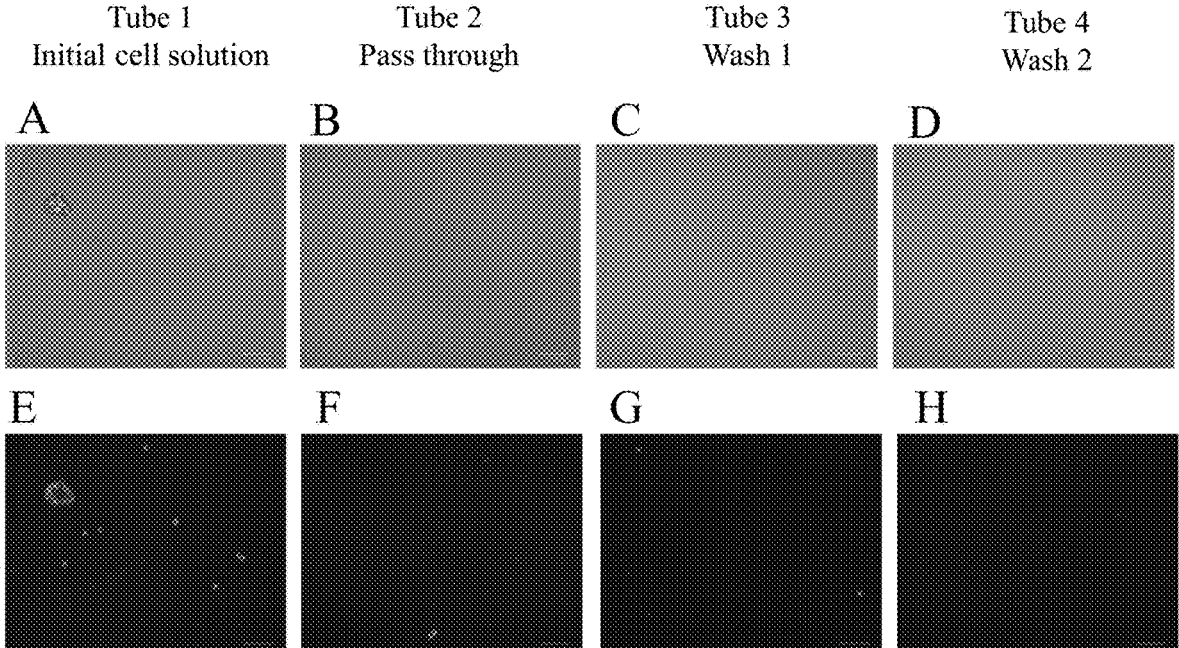
FIG. 8 shows bright field and GFP images of an A549 lung cancer cell line before and after passing approximately $3.0 \times 10^4$ cells through a column prepared with 0.5 ml of 5% 3-Aminopropyltriethoxysilane Bead matrix (A-D). Lung cancer cells are seen under the green fluorescence view (E-H). Most cancer cells were captured by the bead matrix as indicated by minimal number of stained cells in F-G.

For the experiment performed with the same number of beads and less cells, the experiment was performed identical to the described above, except 30 µl, approximately $3.0 \times 10^4$ cells were used, and the volume brought up to 500 µl with 470 µl of PBS. Results can be seen in FIG. 8. Multiple cells can be seen in the Initial Cell Solution, however fewer cells are seen in the Pass-Through, First and Second Wash samples as compared to the experiment using more cells. This again indicates that this cell line may require a higher capacity to improve cell binding.

Example 4. Isolation of Acute Lymphoblastic Leukemia Cells

Approximately $1.0 \times 10^6$ CCRF-SB acute lymphoblastic leukemia cells were stained using the method described above. 100 µl, approximately $1.0 \times 10^5$ stained cells, were added to a tube ("Initial Cell Solution") and the volume brought up to 500 µl with 400 µl PBS. The cells were mixed thoroughly and added to a column of 0.5 ml of either 5% 3-Aminopropyltriethoxysilane or 10% 3-Aminopropyltrimethoxysilane beads, prepared as explained above. The cells were added 100 µl at a time, making sure to avoid air bubbles, and the flow-through collected in a second tube ("Pass-Through"). Once the column had stopped dripping, the column was washed with 500 µl PBS, added 100 µl at a time, making sure to avoid air bubbles, and the flow-through collected in a third tube ("First Wash"). Once the column had stopped dripping, the column was washed a second time with 500 µl PBS, added 100 µl at a time, making sure to avoid air bubbles, and the flow-through collected in a fourth tube ("Second Wash"). Once the column had stopped dripping, the needle was capped and the cells from each of the four tubes were analyzed under a microscope.

Figure 9:
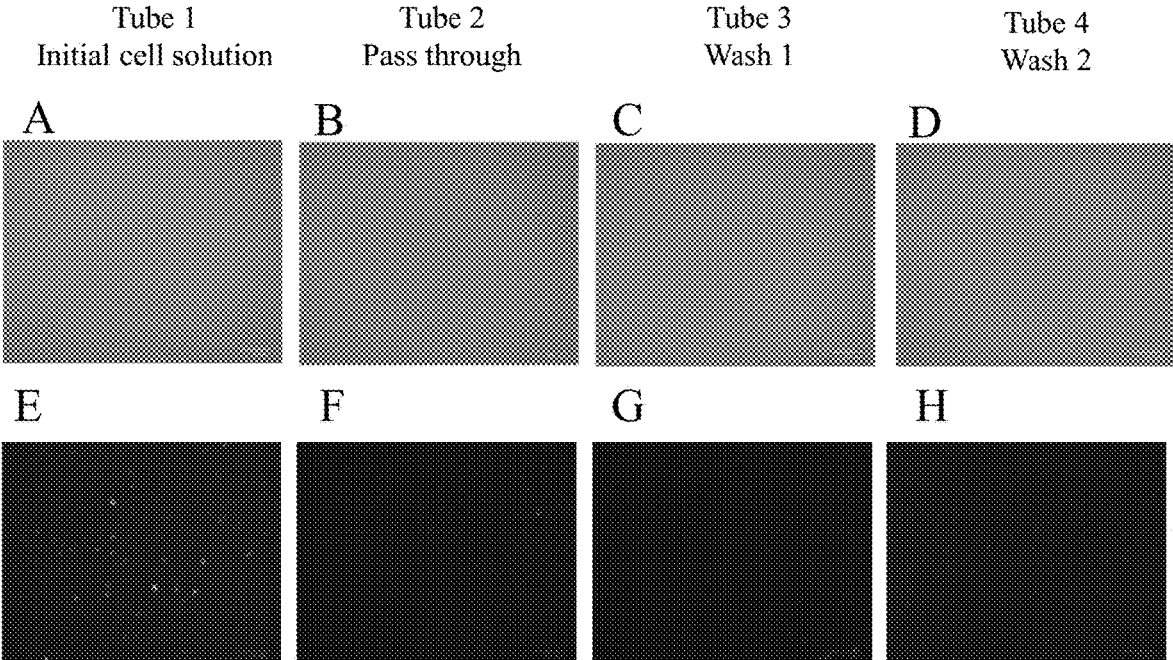
FIG. 9 shows bright field and GFP images of CCRF-SB acute lymphoblastic leukemia (ALL) cells before and after passing approximately $1.0 \times 10^5$ cells through a column prepared with 0.5 ml of 5% 3-Aminopropyltriethoxysilane Bead matrix (A-D). ALL cells are seen under the green fluorescence view (E-H). All cancer cells were captured by the bead matrix as indicated by lack of stained cells in F-G.

FIG. 9 shows a bright field and green fluorescence view of 10 µl of each of the Initial Cell Solution (A and E), the Pass-Through sample (B and F), the First Wash sample (C and G), and the Second Wash sample (D and H) for the acute lymphoblastic leukemia cancer cells passed through the 5% 3-Aminopropyltriethoxysilane bead column. Viable acute lymphoblastic leukemia cancer cells are visualized as green fluorescence when looked at under the microscope with green light due to calcein AM staining. Multiple cells can be seen in the Initial Cell Solution, however minimal cells are seen in the Pass-Through sample, and no cells are seen in each of the First and Second Wash samples. This indicates that the viable acute lymphoblastic leukemia cancer cells remained in the column and were captured by the positively charged 5% 3-Aminopropyltriethoxysilane beads.

Figure 10:
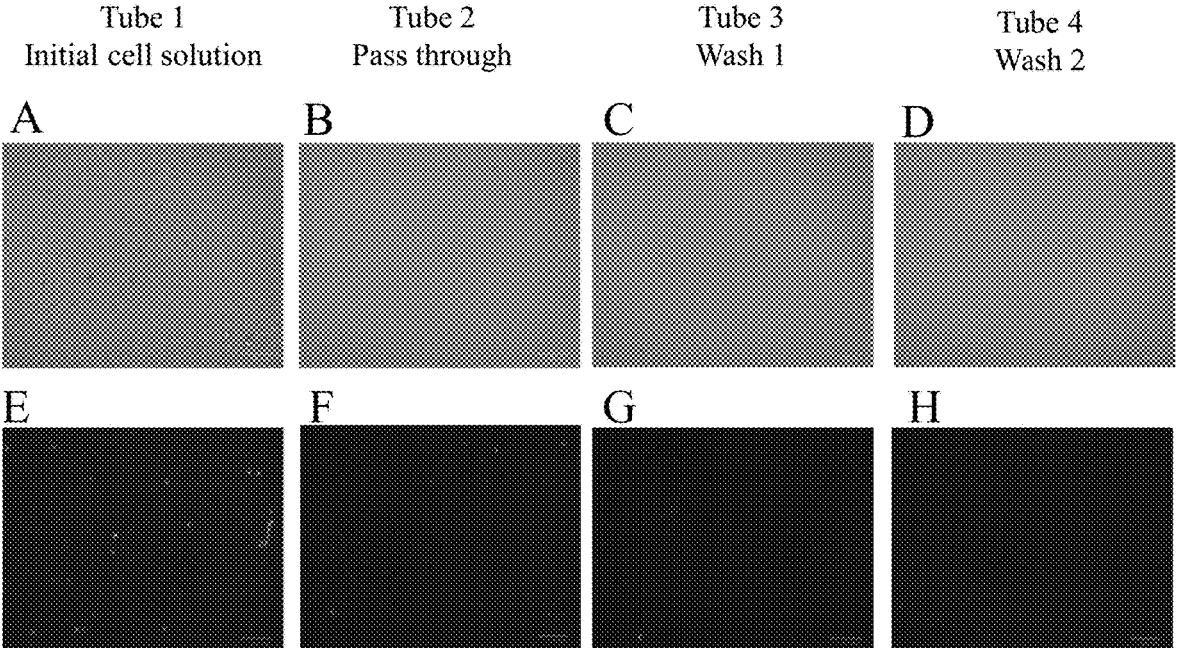
FIG. 10 shows bright field and GFP images of CCRF-SB acute lymphoblastic leukemia cells (ALL) before and after passing approximately $1.0 \times 10^5$ cells through a column prepared with 0.5 ml of 10% 3-Aminopropyltrimethoxysilane Bead matrix (A-D). ALL cells are seen under the green fluorescence view (E-H). Most cancer cells were captured by the bead matrix as indicated by minimal number of stained cells in F-G

FIG. 10 shows a bright field and green fluorescence view of 10 µl of each of the Initial Cell Solution (A and E), the Pass-Through sample (B and F), the First Wash sample (C and G), and the Second Wash sample (D and H) for the acute lymphoblastic leukemia cancer cells passed through the 10% 3-Aminopropyltrimethoxysilane bead column. Viable acute lymphoblastic leukemia cancer cells are visualized as green fluorescence when looked at under the microscope with green light due to calcein AM staining. Multiple cells can be seen in the Initial Cell Solution, however in each of the Pass-Through and First and Second Wash samples, minimal cells are seen, indicating the viable acute lymphoblastic leukemia cancer cells remained in the column and were captured by the positively charged 10% 3-Aminopropyltrimethoxysilane beads.

Each of the 5% 3-Aminopropyltriethoxysilane or 10% 3-Aminopropyltrimethoxysilane bead columns demonstrated similar results for capturing the acute lymphoblastic leukemia cancer cells.

Example 5. Isolation of Cancer Cells in the Presence of Non-Cancerous WBC

To determine whether the positively charged bead matrix is capable of isolating cancer cells from a mixture of cancer and non-cancer cells, SW620 colon cancer cells were mixed with non-cancerous purified white blood cells and the mixture was passed through the column.

Approximately $1.0 \times 10^6$ SW620 colon cancer cells were stained using the method described above and WBC were purified using the blood lysis protocol described above. 100 µl, approximately $1.0 \times 10^5$, stained tumor cells, were mixed with 200 µl WBC in PBS in a tube ("Initial Cell Solution") and the volume brought up to 500 µl with 200 µl PBS. The cells were mixed thoroughly and added to a column of 0.5 ml of either 5% 3-Aminopropyltriethoxysilan or 10% 3-Aminopropyltrimethoxysilane beads, prepared as explained above. The cells were added 100 µl at a time, making sure to avoid air bubbles, and the flow-through collected in a second tube ("Pass-Through"). Once the column had stopped dripping, the column was washed with 500 µl PBS, added 100 µl at a time, making sure to avoid air bubbles, and the flow-through collected in a third tube ("First Wash"). Once the column had stopped dripping, the column was washed a second time with 500 µl PBS, added 100 µl at a time, making sure to avoid air bubbles, and the flow-through collected in a fourth tube ("Second Wash"). Once the column had stopped dripping, the needle was capped and the cells from each of the four tubes were analyzed under a microscope.

Figure 11:
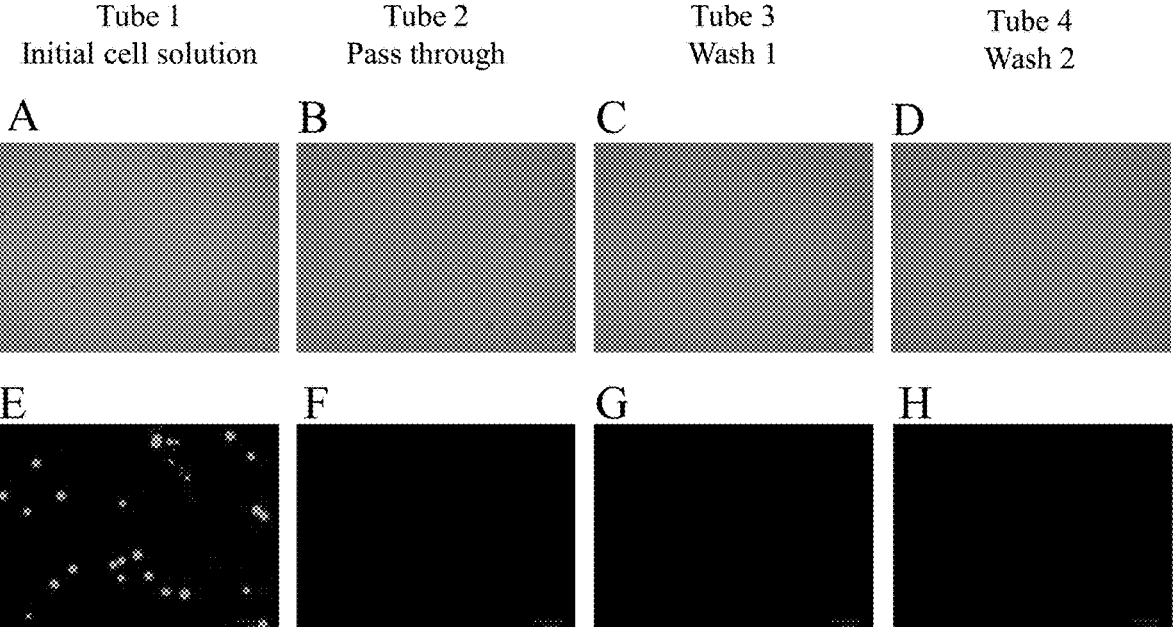
FIG. 11 shows microscopic field view of a mixture of $1.0 \times 10^5$ colon cancer cells and 400 µl non-cancerous WBCs before and after passing through a 5% 3-Aminopropyltri-ethoxysilane Bead matrix (A-D). Colon cancer cells are seen under the green fluorescence view (E-H). All tumor cells were captured by the bead matrix as indicated by lack of stained cells in F-G. The presence of cells in B indicates that non-cancerous WBCs were not captured by the bead matrix.

FIG. 11 shows a bright field and green fluorescence view of 10 µl of each of the Initial Cell Solution (A and E), the Pass-Through sample (B and F), the First Wash sample (C and G), and the Second Wash sample (D and H) for the colon cancer cell/WBC mixture passed through the 5% 3-Aminopropyltriethoxysilane bead column. Both colon cancer cells and WBCs can be seen in the bright field view. Viable colon cancer cells are visualized as green fluorescence when looked at under the microscope with green light due to calcein AM staining. Multiple viable colon cancer cells can be seen in the Initial Cell Solution, however no viable colon cancer cells are seen in the Pass-Through, First, and Second Wash samples. WBC can be seen in the bright field view for each of the Pass-Through, First, and Second Wash samples, on the other hand. This indicates that the viable colon cancer cells remained in the column and were captured by the positively charged 5% 3-Aminopropyltriethoxysilane beads, whereas the non-cancerous WBC were not captured.

Figure 12:
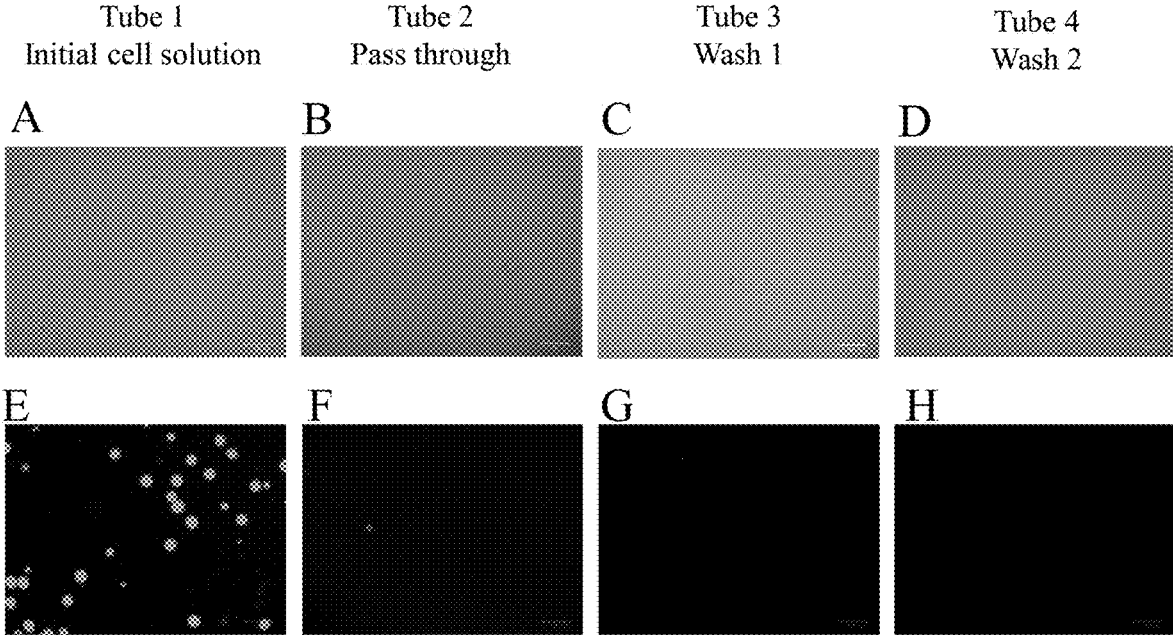
FIG. 12 shows microscopic field view of a mixture of $1.0 \times 10^6$ colon cancer cells and 200 µl non-cancerous WBCs before and after passing through a 3-Aminopropyltriethox-ysilane Bead matrix (A-D). Colon cancer cells are seen under the green fluorescence view (E-H). All tumor cells were captured by the bead matrix as indicated by lack of stained cells in F-G. The presence of cells in B indicates that non-cancerous WBCs were not captured by the bead matrix.

The experiment was repeated with an increase in the amount of WBC in the mixture. The experiment was performed identical to the described above, except 400 µl of WBC in PBS. Results can be seen in FIG. 12. Again, no viable colon cancer cells are seen in the Pass-Through, First, and Second Wash samples and WBC can be seen in the bright field view for each of the Pass-Through, First, and Second Wash samples. This confirms that the viable colon cancer cells remained in the column and were captured by the positively charged 5% 3-Aminopropyltriethoxysilane beads, whereas the non-cancerous WBC were not captured.

Example 7. Isolation of Cancer Cells Using a Mini-Column

A single capillary tube containing positively charged 10% 3-Aminopropyltrimethoxysilane beads, prepared as previously described, was used as a "mini-column" for each run. The cells were collected and stained as described previously. 100 µl, approximately $1.0 \times 10^5$ stained cells, were added to a tube ("Initial Cell Solution") and the volume brought up to 500 µl with 400 µl PBS. The cells were mixed thoroughly and added to the mini-column using a micropipette with a long tip. The cells were added 100 µl at a time, making sure to avoid air bubbles, and the flow-through collected in a second tube ("Pass-Through"). Once the mini-column stopped running, the mini-column was washed with 500 µl PBS, added 100 µl at a time, making sure to avoid air bubbles, and the flow-through collected in a third tube ("First Wash"). Once the mini-column had stopped running, the mini-column was washed a second time with 500 µl PBS, added 100 µl at a time, making sure to avoid air bubbles, and the flow-through collected in a fourth tube ("Second Wash"). Once the mini-column had stopped running, the mini-column was analyzed under a microscope to see an adherence of green-fluorescing cells attached to the positively charged glass beads.

Figure 13:
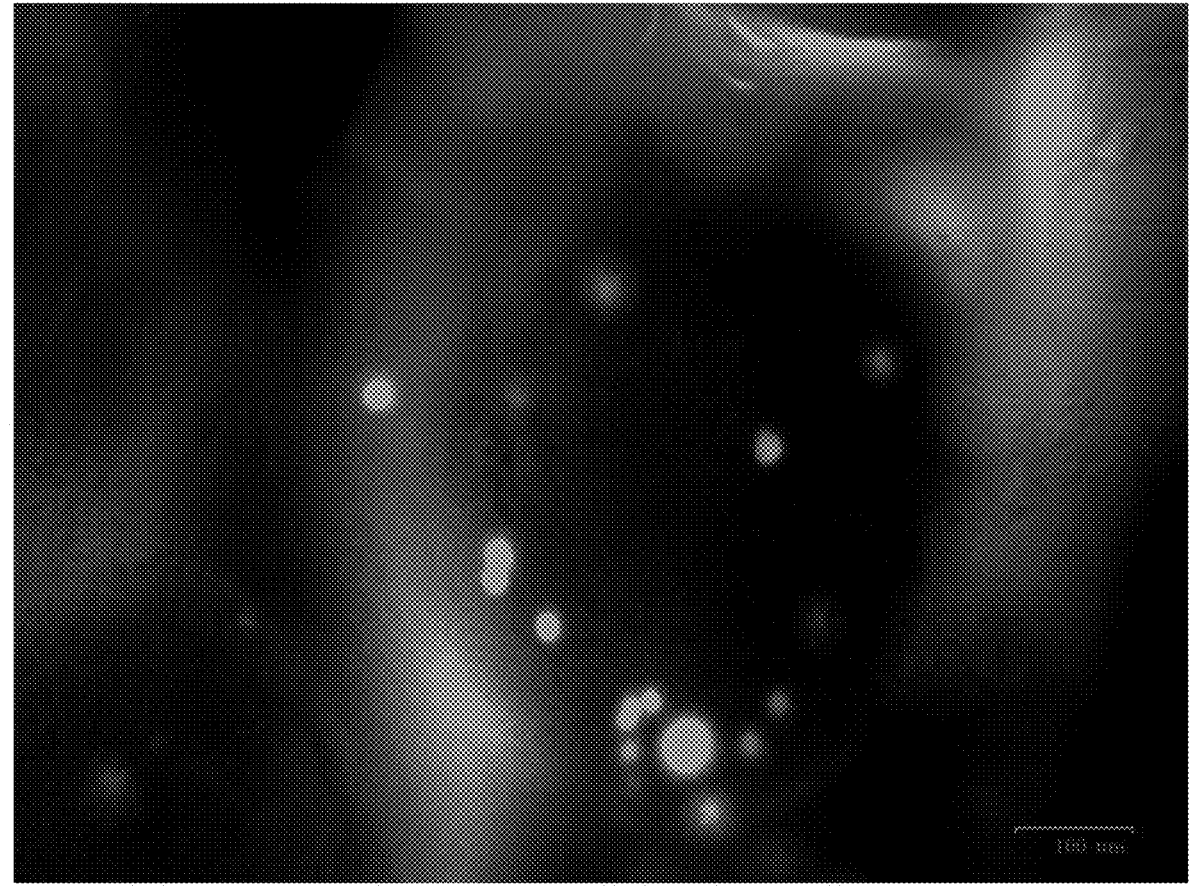
FIG. 13 shows captured breast cancer cells on positively charged glass beads in a transparent glass 1.5 mm mini-column. The cells are clearly able to be visualized, analyzed, and evaluated by fluorescently labeled antibody markers.

FIG. 13 shows a green fluorescence view of the captured breast cancer cells on positively charged glass beads in the transparent glass 1.5 mm mini-column. The narrow diameter of the capillary tubes allows the cells to be clearly visualized, analyzed, and evaluated by fluorescently labeled antibody markers to determine the tissue of origin.

Example 8. Measuring Bead Capacity

In order to determine the number of beads required for downstream applications such as preparing vaccines for example, bead capacity was measured. One amine coated glass bead having a diameter of between 1.7 and 2.5 mm and prepared as described above, was incubated in 1 ml of PBS with $1 \times 10^6$ cells for 1 hour. Following incubation, the singular bead was washed 3 times in PBS. 40 µl of 1% SDS was added to the bead to lyse cells and incubated for 30 min. Following incubation, the bead and lysed cells were centrifuged at 10,000×g for 5 min. The absorbance of the supernatant was read at 280 nm on the nanodrop and the value was compared to the standard curve prepared as described below. This procedure was then repeated using 5 beads.

Figure 15:
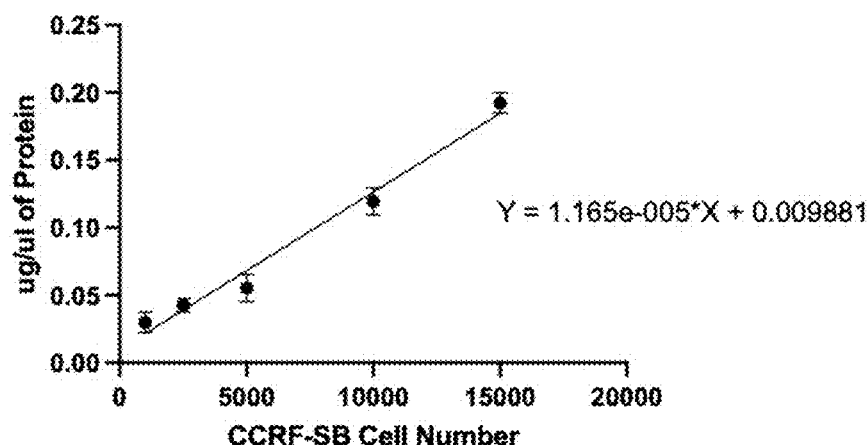
FIG. 15 shows a standard curve of cell number vs protein concentration established using the CCRF-SB cell line used to determine bead capacity.

A standard curve was established using CCRF-SB cell line (Human Acute Lymphoblastic Leukemia). Set numbers of cells $1 \times 10^3$, $2.5 \times 10^3$, $5 \times 10^3$, $1 \times 10^4$ and $1.5 \times 10^4$ in 20 µl of PBS were lysed with 20 µl of 1% SDS. After 30 min incubation, tubes were centrifuged at 10,000×g for 5 min. The absorbance of the supernatant was read at 280 nm on the nanodrop and µg/µl of protein vs cell number was graphed (FIG. 15).

Results

Cell lysate generated from 1 Bead had an absorbance at 280 nm of 0.02725. The Equation generated from the standard curve was used to determine cell number, i.e., $Y = 1.165e{-}005*X + 0.009881$. Accordingly, 1 bead had a capacity of 1490.90 cells.

5 Beads had an absorbance at 280 nm of 0.0876. The Equation generated from the curve was used to determine cell number. Accordingly, 5 Beads had a capacity of 6676.88, therefore 1 bead had a capacity of 1335.38 cells.

Conclusion

From this data, it was concluded that 1 amine coated charge bead binds roughly 1400 cells. This information can be used for downstream applications, for example, $1\times10^6$ cells are required to prepare sufficient lysate for the tumor lysate vaccines described herein. Therefore, roughly 750 beads are required to capture $1\times10^6$ cells, and a column containing equal to or greater than 750 beads is sufficient to capture sufficient leukemia or other blood cancer cells from a patient's blood to produce an effective therapeutic cancer vaccine.

Example 9. Quantification of Circulating Cancer Cells

For diagnostic use, the nucleic acid content of the lysate i.e., the mRNA copy number determined by quantitative RT-PCR may be used for determination of the number of tumor cells bound to each bead.

Amine coated glass beads were prepared as described herein and functionalized with 10% 3-Aminopropyltriethoxysilane. 10 million human PBMC cells, 10 million human PBMC cells spiked with 160 human SKOV3 breast cancer cells, and 160 human SKOV3 cells were prepared, each in a final volume of 50 µl in PBS. Cells were transferred into U-bottomed wells in a 96 well plate with a single glass bead having a diameter of between 1.7 and 2.5 mm in each well. The plate was shaken for one hour at room temperature at 100 rpm. The beads were picked up with forceps and washed 3× with PBS. The beads were then put into a PCR tube and lysed with 50 µl lysis buffer. 10 µl of cell lysate was used for reverse transcript reaction in a final volume of 20 µl. 1 microliter of the reverse transcript reaction was used for quantitative PCR analysis.

Figure 16:
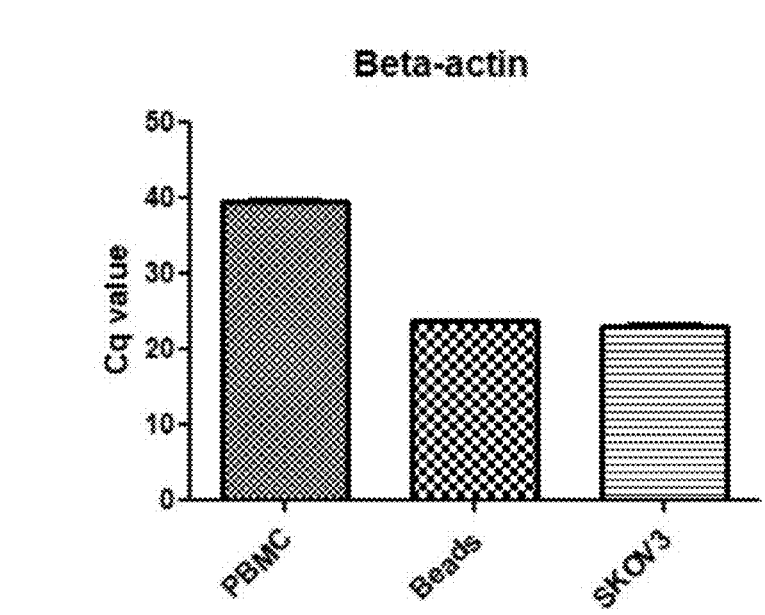
FIG. 16 shows number of PCR cycles to detect (A) beta-actin and (B) Her2 in unbound PBMCs (PBMC), bead
Figure 16:
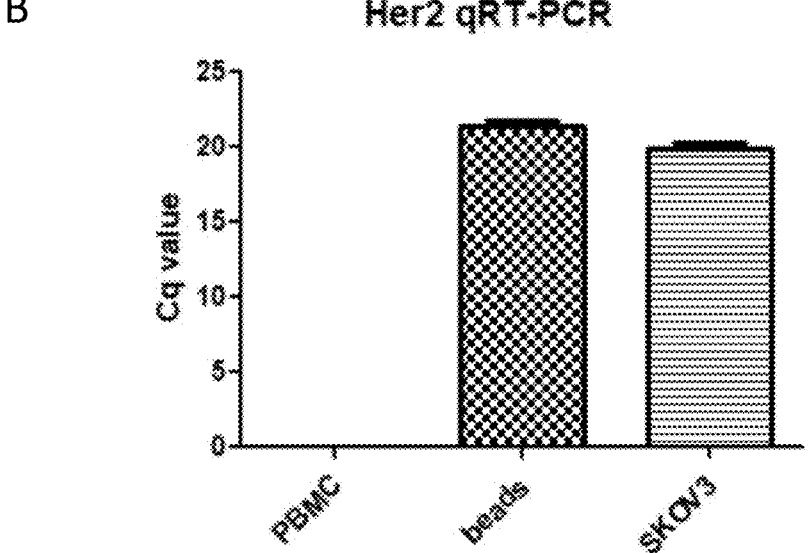

Using Beta-Actin PCR primers (a housekeeping gene) the number of cycles of amplification required to observe a PCR product were measured (FIG. 16A). Similarly, using Her2 PCR primers the number of cycles of amplification required to observe a PCR product were measured (FIG. 16B).

Using the number of cycles, a standard curve was produced (FIG. 17) that demonstrated that a single human breast cancer cell can be determined by quantitative PCR analysis in about 37 cycles. This standard curve can be used to determine numbers of breast cancer cells in a sample. Similar curves can be prepared for different cancer samples following the protocol described in the flow chart of FIG. 18 (white boxes) to quantify the number of cancer cells in a sample.

Example 10. Detection and Identification of Circulating Cancer Cells in Patient Sample Using the protocol in the flow chart of FIG. 18 (white and gray boxes), the methods described herein can be used to quantify, detect, and identify cancer cells in a patient. PBMCs from 7.5 ml patient blood were resuspended in 200 µl PBS. 10 µl of the cells were used for circulating cancer cell isolation with two glass beads in 100 µl of PBS. After 1 hour incubation with 100 rpm shaking at room temperature, the glass beads were isolated and washed 3 times with PBS. 10 µl of the original PBMCs, the PBMC from circulating cancer cell isolation, and the glass beads were all lysed with 50 µl lysis buffer. 10 µl of the lysate was used for first strand cDNA synthesis in a 20 µl reaction. First strand cDNA was diluted 10 times and 1 µl was used for quantitative PCR amplification in a 20 µl reaction.

Results

As can be seen in FIG. 19, these results show clearly that the circulating cancer cells captured by the beads from the patient's blood sample were breast cancer cells expressing Her2 and Beta-Actin and only breast cancer cells were captured, since the circulating cancer cells captured showed no contamination with lymphocytes, the vast majority of cells in the patient blood sample, since the highly sensitive CD45 PCR assay was absolutely negative (FIG. 19C).

What is claimed is:

1. A method of removing cancer cells from a biological sample, comprising:
   a) passing a biological sample comprising cancer cells obtained from a subject over an isolation matrix comprising a positively charged surface, wherein the positively charged surface comprises glass that is functionalized with a positively charged functional group selected from the group consisting of an amine, an aldehyde, polyethylenimine (PEI), a guanidine group, and a combination thereof; and
   b) collecting the biological sample that flows through the isolation matrix comprising the positively charged surface in a first aliquot,
   wherein the cancer cells bind to the isolation matrix.

2. The method of claim 1, wherein the positively charged surface is selected from a bead, a microparticle, a capillary tube, a blood collection tube, a microscope slide, and a microscope slide coverslip.

3. The method of claim 1, wherein the biological sample comprises blood.

4. The method of claim 1, further comprising lysing the cancer cells bound to the isolation matrix, thereby obtaining a cancer cell lysate.

5. The method of claim 1, wherein the first aliquot is administered back into the subject.

6. The method of claim 1, further comprising detecting the presence of the cancer cells in the biological sample via cell staining or cell lysis followed by PCR amplification.

7. The method of claim 1, wherein the positively charged surface is a glass bead functionalized with an amine, an aldehyde, PEI, or a guanidine group.

8. The method of claim 7, wherein the positively charged surface is a glass bead functionalized with an amine.

9. The method of claim 7, wherein the positively charged surface is a glass bead functionalized with an aldehyde.

10. The method of claim 7, wherein the positively charged surface is a glass bead functionalized with PEI.

11. The method of claim 7, wherein the positively charged surface is a glass bead functionalized with a guanidine group.

12. A method of detecting a cancer cell in a patient, comprising:
   a) passing a biological sample from the patient through a functionalized glass capillary tube or an isolation matrix of functionalized glass microspheres, wherein the functionalized glass capillary tube or the functionalized glass microspheres comprise amine, polyethylenimine (PEI), and/or guanidine groups that are attached to the glass capillary tube or glass microsphere via a siloxane bond, and wherein the functionalized glass capillary tube or the functionalized glass microspheres bind cancer cells;

b) eluting the biological sample that flows through the functionalized glass capillary tube or the isolation matrix; and c) detecting the presence of a cancer cell bound to the functionalized glass capillary tube or functionalized glass microspheres.

13. The method of claim 12, wherein the patient has a hematological cancer or a malignant cancer.

14. The method of claim 12, wherein the biological sample is passed through the isolation matrix of functionalized glass microspheres.

15. A method of binding a cancer cell from a biological sample, comprising:

a) contacting a biological sample comprising a cancer cell with an isolation matrix comprising glass beads having surfaces that are functionalized with a positively charged functional group which may be any one or more of an amine, an aldehyde, polyethyleneimine (PEI), or a guanidine group;

b) washing the isolation matrix to remove the biological sample from the isolation matrix, wherein the cancer cell binds to the isolation matrix;

c) lysing the cancer cell, thereby providing a lysate; and d) detecting in the lysate one or more nucleic acids.

16. The method of claim 15, wherein the biological sample is obtained from a subject suspected of having a cancer.

17. The method of claim 16, wherein the cancer is a hematological cancer or comprises a solid tumor.

18. The method of claim 15, wherein detecting in the lysate one or more nucleic acids comprises performing RT-PCR on mRNA isolated from the lysate.

*    *    *    *    *